(12) United States Patent
Wang et al.

(10) Patent No.: US 8,295,435 B2
(45) Date of Patent: Oct. 23, 2012

(54) CARDIAC TARGET TRACKING

(75) Inventors: James Wang, Palo Alto, CA (US);
Dongshan Fu, Santa Clara, CA (US);
Calvin R. Maurer, Jr., Mountain View, CA (US)

(73) Assignee: Accuray Incorporated, Sunnyvale, CA (US)

( * ) Notice: Subject to any disclaimer, the term of this patent is extended or adjusted under 35 U.S.C. 154(b) by 278 days.

(21) Appl. No.: 12/354,710

(22) Filed: Jan. 15, 2009

(65) Prior Publication Data

US 2009/0180589 A1 Jul. 16, 2009

Related U.S. Application Data

(60) Provisional application No. 61/011,429, filed on Jan. 16, 2008.

(51) Int. Cl.
*A61B 6/00* (2006.01)
(52) U.S. Cl. ............... 378/65; 378/8; 378/95; 600/427; 600/428
(58) Field of Classification Search ............... 378/8, 65, 378/95; 600/427, 428
See application file for complete search history.

(56) References Cited

U.S. PATENT DOCUMENTS

| | | | |
|---|---|---|---|
| 4,452,252 A | 6/1984 | Sackner | |
| 4,583,538 A | 4/1986 | Onik et al. | |
| 5,067,981 A | 11/1991 | Hooykaas | |
| 5,207,223 A | 5/1993 | Adler | |
| 5,222,499 A | 6/1993 | Allen et al. | |
| 5,447,154 A | 9/1995 | Cinquin et al. | |
| 5,457,728 A | 10/1995 | Whiting et al. | |
| 5,537,452 A | 7/1996 | Shepherd et al. | |
| 5,588,430 A | 12/1996 | Bova et al. | |
| 5,622,187 A | 4/1997 | Carol | |
| 5,727,554 A | 3/1998 | Kalend et al. | |
| 5,797,849 A | 8/1998 | Vesely et al. | |
| 5,901,199 A | 5/1999 | Murphy et al. | |
| 5,971,997 A | 10/1999 | Guthrie et al. | |
| 6,006,126 A | 12/1999 | Cosman | |
| 6,076,005 A | 6/2000 | Sontag et al. | |
| 6,120,453 A | 9/2000 | Sharp | |
| 6,144,875 A | 11/2000 | Schweikard et al. | |
| 6,307,914 B1 | 10/2001 | Kunieda et al. | |
| 6,314,312 B1 | 11/2001 | Wessels et al. | |

(Continued)

FOREIGN PATENT DOCUMENTS

WO WO99/35966 7/1999

(Continued)

OTHER PUBLICATIONS

PCT International Search Report and Written Opinion of the International Searching Authority, PCT/US09/031280 filed Jan. 16, 2009, mailed Mar. 3, 2009.

(Continued)

*Primary Examiner* — Hoon Song
*Assistant Examiner* — Mona M Sanei
(74) *Attorney, Agent, or Firm* — Lowenstein Sandler PC

(57) ABSTRACT

Systems and methods for tracking cardiac targets are disclosed. The cardiac targets may be tracked dynamically. The process may include registering a cardiac target at different phases of a cardiac cycle. Movement of the cardiac target can be determined by correlating respiratory motion and cardiac pumping motion. Radiation treatment can then be delivered to the cardiac target taking into account the movement of the cardiac target.

4 Claims, 18 Drawing Sheets

U.S. PATENT DOCUMENTS

| | | |
|---|---|---|
| 6,501,981 B1 | 12/2002 | Schweikard et al. |
| 6,501,982 B1 | 12/2002 | Ruchti et al. |
| 6,516,046 B1 | 2/2003 | Froehlich et al. |
| 6,889,695 B2 | 5/2005 | Pankratov et al. |
| 7,171,257 B2 | 1/2007 | Thomson |
| 7,445,605 B2 | 11/2008 | Overall et al. |
| 7,558,402 B2 | 7/2009 | Zhou et al. |
| 7,645,276 B2 | 1/2010 | Pankratov et al. |
| 2002/0193685 A1 | 12/2002 | Mate et al. |
| 2004/0015073 A1* | 1/2004 | Schell et al. ............ 600/411 |
| 2004/0131150 A1 | 7/2004 | Pankratov et al. |
| 2004/0225332 A1 | 11/2004 | Gebhardt et al. |
| 2004/0267113 A1 | 12/2004 | Thomson |
| 2005/0053267 A1 | 3/2005 | Mostafavi |
| 2005/0161051 A1 | 7/2005 | Pankratov et al. |
| 2005/0171396 A1 | 8/2005 | Pankratov et al. |
| 2005/0228255 A1 | 10/2005 | Saracen et al. |
| 2006/0256915 A1 | 11/2006 | Otto et al. |
| 2008/0177279 A1 | 7/2008 | Sumanaweera et al. |
| 2008/0177280 A1 | 7/2008 | Adler et al. |
| 2008/0317204 A1 | 12/2008 | Sumanaweera et al. |
| 2009/0041188 A1 | 2/2009 | Keall et al. |
| 2009/0080610 A1 | 3/2009 | Sumanaweera et al. |
| 2010/0160775 A1 | 6/2010 | Pankratov et al. |

FOREIGN PATENT DOCUMENTS

| | | |
|---|---|---|
| WO | WO03/005893 A2 | 1/2003 |
| WO | WO2004/062479 | 7/2004 |
| WO | WO2005/000102 A2 | 1/2005 |
| WO | WO2008/086430 A1 | 7/2008 |
| WO | WO2008/086434 A3 | 7/2008 |
| WO | WO2008/115830 A3 | 9/2008 |
| WO | WO2009/042842 A1 | 4/2009 |

OTHER PUBLICATIONS

Schweikard A. et al., "Treatment Planning for a Radiosurgical System with General Kinematics", Proceedings of the International Conference on Robotics and Automation, San Diego, May 8-13, 1994, Los Alamitos, IEEE Comp. Soc. Press, US, vol. 2 Conf. 11, May 8, 1994, pp. 1720-1727, XP000478538, ISBN: 0-8186-5332-9, Section 2.

Bardash M., et al., "Rapid Dose Calculations for Stereotactic Radiosurgery", Medical Physics, AIP, Melville, NY, US, vol. 19, No. 4, Jul. 1, 1992, pp. 965-970, XP000309447, ISSN: 0094-2405.

Achim Schweikard, et al. "Robotic Motion Compensation for Respiratory Movement During Radiosurgery", Computer Aided Surgery, 5:263-277 (2000).

Toni Neicu, et al., "Synchronized Moving Aperture Radiation Therapy (SMART): average Tumour Trajectory for Lung Patients", Phys. Med. Biol. 48 (2003) 587-598.

Gregory C. Sharp et al., "Prediction of Respiratory Tumour Motion for Real-Time Image-Guided Radiotherapy", Phys. Med. Biol. 49 (2004) 425-440.

Coste-Manière, È., "Robotic whole body stereotactic radiosurgery: clinical advantages of the CyberKnife® integrated system", The International Journal of Medical Robotics+Computer Assisted Surgery, 2005, www.roboticpublications.com, pp. 28-39.

\* cited by examiner

CARDIAC TARGET TRACKING

RELATED APPLICATIONS

This application claims the benefit of the filing date of U.S. Provisional Application No. 61/011,429, filed Jan. 16, 2008, which is incorporated herein by reference in its entirety.

TECHNICAL FIELD

This invention relates to the field of radiotherapy and radiosurgery treatment and, in particular, to dynamic tracking of cardiac targets.

BACKGROUND

Pathological anatomies such as tumors and lesions can be treated with an invasive procedure, such as surgery, but can be harmful and full of risks for the patient. A non-invasive method to treat a pathological anatomy (e.g., tumor, lesion, vascular malformation, nerve disorder, etc.) is external beam radiation therapy. In one type of external beam radiation therapy, an external radiation source is used to direct a sequence of x-ray beams at a pathological anatomy from multiple angles, with the patient positioned so the pathological anatomy is at the center of rotation (isocenter) of the beam. As the angle of the radiation source changes, every beam passes through the pathological anatomy, but passes through a different area of healthy tissue on its way to the pathological anatomy. As a result, the cumulative radiation dose at the pathological anatomy is high and the average radiation dose to healthy tissue is low.

The term "radiotherapy" refers to a procedure in which radiation is applied to a target region for therapeutic, rather than necrotic, purposes. The amount of radiation utilized in radiotherapy treatment sessions is typically about an order of magnitude smaller, as compared to the amount used in a radiosurgery session. Radiotherapy is typically characterized by a low dose per treatment (e.g., 100-200 centigray (cGy)), short treatment times (e.g., 10 to 30 minutes per treatment) and hyperfractionation (e.g., 30 to 45 days of treatment). For convenience, the term "radiation treatment" is used herein to mean radiosurgery and/or radiotherapy unless otherwise noted.

As one example, atrial fibrillation is a medical condition characterized by an abnormally rapid and irregular heart rhythm, because of uncoordinated contractions of the atria (i.e. the upper chambers of the heart.) A normal, steady heart rhythm typically beats 60-80 times a minute. In cases of atrial fibrillation, the rate of atrial impulses can range from 300-600 beats per minute (bpm), and the resulting ventricular heartbeat is often as high as 150 bpm or above. One conventional treatment for atrial fibrillation includes an open heart procedure involving incisions and ablations of areas of the atria to block the re-entry pathways that cause atrial fibrillation. However, when performing the procedure using external beam radiation therapy, it is difficult to track tumor motion that results from cardiac or respiratory motion, such as during treatment of atrial fibrillation.

In addition, there are many other medical applications where it is useful to accurately track the motion of a moving target region (pathological anatomy) in the human anatomy. For example, in radiosurgery, it is useful to accurately locate and track the motion of a target region, due to respiratory and other patient motions during the treatment.

BRIEF DESCRIPTION OF THE DRAWINGS

Embodiments of the invention are described by way of example with reference to the accompanying drawings, wherein.

DETAILED DESCRIPTION

Figure 1:
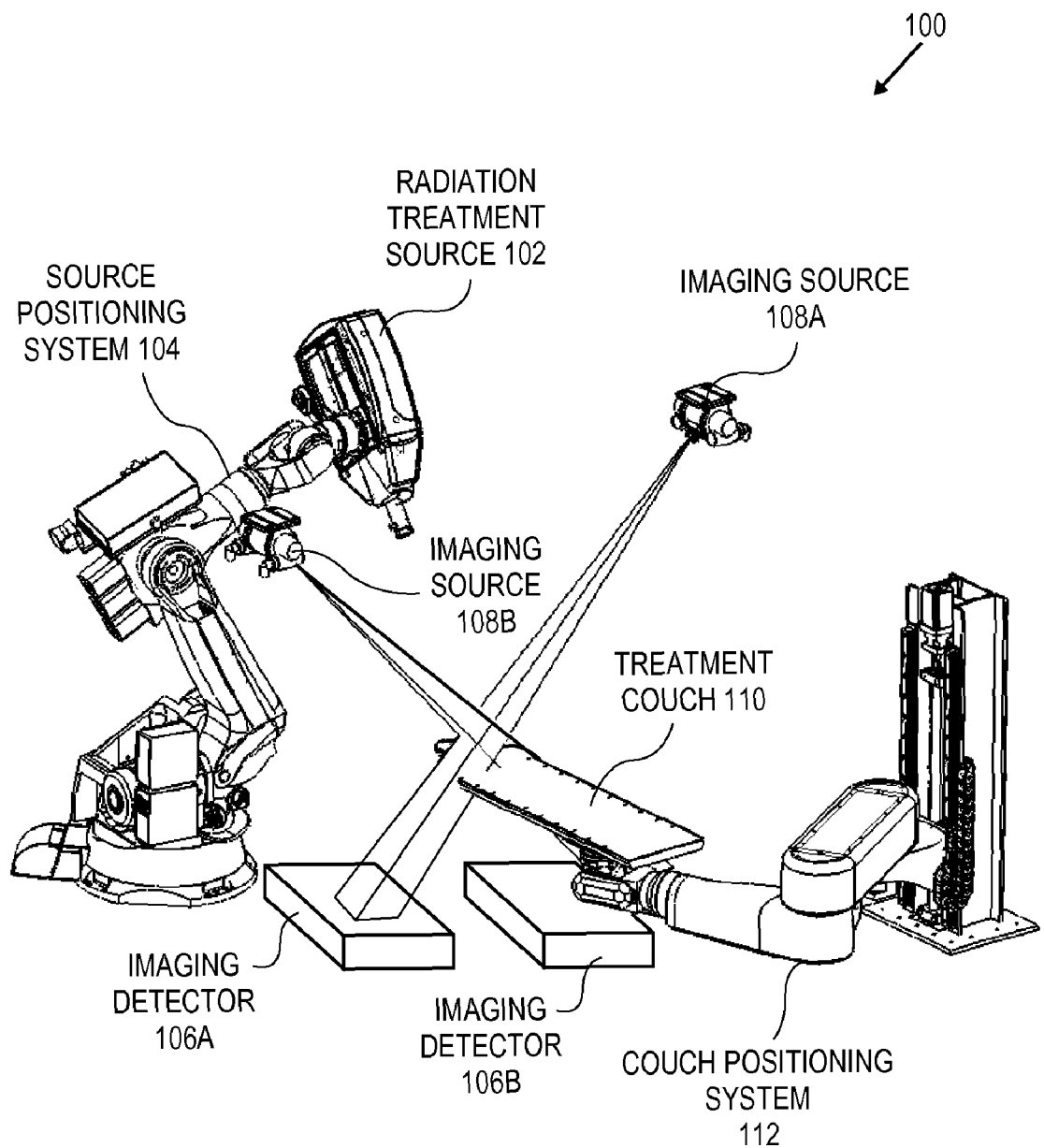
FIG. 1 is a perspective view of a radiation treatment delivery system in accordance with one embodiment of the invention.

The following description sets forth numerous specific details such as examples of specific systems, components, methods, and so forth, in order to provide a good understanding of several embodiments of the present invention. It will be apparent to one skilled in the art, however, that at least some embodiments of the present invention may be practiced without these specific details. In other instances, well-known components or methods are not described in detail or are presented in simple block diagram format in order to avoid unnecessarily obscuring the present invention. Thus, the specific details set forth are merely exemplary. Particular implementations may vary from these exemplary details and still be contemplated to be within the spirit and scope of the present invention.

Embodiments of the present invention include various operations, which will be described below. These operations may be performed by hardware components, software, firmware, or a combination thereof. Additionally, the interconnection between circuit components or blocks may be shown as buses or as single signal lines. Each of the buses may alternatively be one or more single signal lines and each of the single signal lines may alternatively be buses.

Certain embodiments may be implemented as a computer program product which may include instructions stored on a machine-readable medium. These instructions may be used to program a general-purpose or special-purpose processor to perform the described operations. A machine-readable medium includes any mechanism for storing or transmitting information in a form (e.g., software, processing application) readable by a machine (e.g., a computer). The machine-readable medium may include, but is not limited to, magnetic storage media (e.g., floppy diskette); optical storage media (e.g., CD-ROM); magneto-optical storage media; read-only memory (ROM); random-access memory (RAM); erasable programmable memory (e.g., EPROM and EEPROM); flash memory; electrical, optical, acoustical, or other form of propagated signal (e.g., carrier waves, infrared signals, digital signals, etc.); or another type of media suitable for storing electronic instructions.

Additionally, some embodiments may be practiced in distributed computing environments where the machine-readable medium is stored on and/or executed by more than one computer system. In addition, the information transferred between computer systems may either be pulled or pushed across the communication medium connecting the computer systems such as in a remote diagnosis or monitoring system. In remote diagnosis or monitoring, a user may diagnose or monitor a patient despite the existence of a physical separation between the user and the patient. In addition, the treatment delivery system may be remote from the treatment planning system.

Unless stated otherwise as apparent from the following discussion, it will be appreciated that terms such as "processing," "registering," "determining," "generating," "correlating" or the like may refer to the actions and processes of a computer system, or similar electronic computing device, that manipulates and transforms data represented as physical (e.g., electronic) quantities within the computer system's registers and memories into other data similarly represented as physical within the computer system memories or registers or other such information storage, transmission or display devices. Embodiments of the method described herein may be implemented using computer software. If written in a programming language conforming to a recognized standard, sequences of instructions designed to implement the methods can be compiled for execution on a variety of hardware platforms and for interface to a variety of operating systems. In addition, embodiments of the present invention are not described with reference to any particular programming language. It will be appreciated that a variety of programming languages may be used to implement embodiments of the present invention.

Some portions of the description that follow are presented in terms of algorithms and symbolic representations of operations on data bits that may be stored within a memory and operated on by a processor. These algorithmic descriptions and representations are the means used by those skilled in the art to effectively convey their work. An algorithm is generally conceived to be a self-consistent sequence of acts leading to a desired result. The acts are those requiring manipulation of quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, parameters, or the like.

Embodiments of a method and apparatus are described to track a cardiac target movement based on respiratory motion and cardiac pumping motion of a patient. In one embodiment, a method and system are presented to correlate respiration movements and cardiac movements (such as heartbeat) of a patient to track the location of the cardiac target. The model can then be used to deliver radiation treatment more effectively to the target.

FIG. 1 is a perspective view of an image guided radiation treatment delivery system 100, in accordance with one embodiment of the invention. The illustrated embodiment of the radiation treatment delivery system 100 includes a radiation treatment source 102, a source positioning system 104, imaging detectors 106A and 106B (collectively 106, also referred to as imagers), imaging sources 108A and 108B, a treatment couch 110 and a couch positioning system 112.

System 100 may be used to perform radiotherapy or radiosurgery to treat a cardiac target within a patient. During radiation treatment, the patient rests on treatment couch 110, which is maneuvered to position a volume of interest ("VOI") within a patient to a preset position or within an operating range accessible to radiation treatment source 102 (e.g., field of view). Similarly, radiation treatment source 102 is maneuvered with multiple degrees of freedom (e.g., rotational and translation freedom) to one or more locations during delivery of a treatment plan. At each location, radiation treatment source 102 may deliver a dose of radiation as prescribed by a treatment plan.

Imaging sources 108 and imaging detectors 106 are part of an image guidance system that provides control over the position of treatment couch 110 and/or radiation treatment source 102 to position and align radiation treatment source 102 with the target VOI within the patient.

In one embodiment, radiation treatment delivery system 100 may be an image-guided, robotic-based radiation treatment system such as the CYBERKNIFE® system developed by Accuray Incorporated of Sunnyvale, Calif. In FIG. 1, radiation treatment source 102 may be a linear accelerator ("LINAC") mounted on the end of the source positioning system 104 (e.g., robotic arm) having multiple (e.g., 5 or more) degrees of freedom in order to position the LINAC to irradiate a pathological anatomy (target region or volume) with beams delivered from many angles in an operating volume (e.g., a sphere) around the patient. Treatment may involve beam paths with a single isocenter (point of convergence), multiple isocenters, or with a non-isocentric approach (i.e., the beams need only intersect with the pathological target volume and do not necessarily converge on a single point, or isocenter, within the target). Treatment can be delivered in either a single session (non-fraction) or in a small number of sessions (hypo-fractionation) as determined during treatment planning. With radiation treatment delivery system 100, in one embodiment, radiation beams may be delivered according to the treatment plan without fixing the patient to a rigid, external frame to register the intra-operative position of the target volume within the position of the target volume during the pre-operative treatment planning phase.

Imaging sources 108A and 108B and imaging detectors (imagers) 106A and 106B may form an imaging system. In one embodiment, imaging sources 108A and 108B are x-ray sources. In one embodiment, for example, two imaging sources 108A and 108B may be nominally aligned to project x-ray beams through a patient from two differing angular positions (e.g., separated by 90 degrees, 45 degrees, etc.) and aimed through the patient on treatment couch 110 toward respective detectors 106A 106B. In another embodiment, a single large imager can be used that would be illuminated by each x-ray imaging source. Alternatively, other numbers and configurations of imaging sources and detectors may be used. The imaging detectors 106 are illustrated as being flat (i.e., parallel to the floor), but the imaging detectors 106 may, alternatively, be angled.

A digital processing system may implement algorithms to register images obtained from the imaging system with pre-operative treatment planning in order to align the patient on the treatment couch 110 with the radiation delivery system 100, and to precisely position the radiation treatment source 102 with respect to the target volume. Registration and alignment techniques are known in the art; accordingly, a detailed description is not provided.

In the illustrated embodiment, treatment couch 110 is coupled to a couch position system 112 (e.g., robotic couch arm) having multiple (e.g., 5 or more) degrees of freedom, such as the ROBOCOUCH® treatment couch, developed by Accuray Incorporated. Couch position system 112 may have five rotational degrees freedom and one substantially vertical, linear degree of freedom. Alternatively, couch positioning system 112 may have six rotational degrees of freedom and one substantially vertical, linear degree of freedom or at least four rotational degrees of freedom. Couch positioning system 112 may be vertically mounted to a column or wall, or horizontally mounted to a pedestal, floor or ceiling. Alternatively, the treatment couch 112 may be a component of another mechanical mechanism, such as the AXUM® treatment couch developed by Accuray Incorporated, or be another type of conventional treatment table known to those of ordinary skill in the art.

Figure 2:
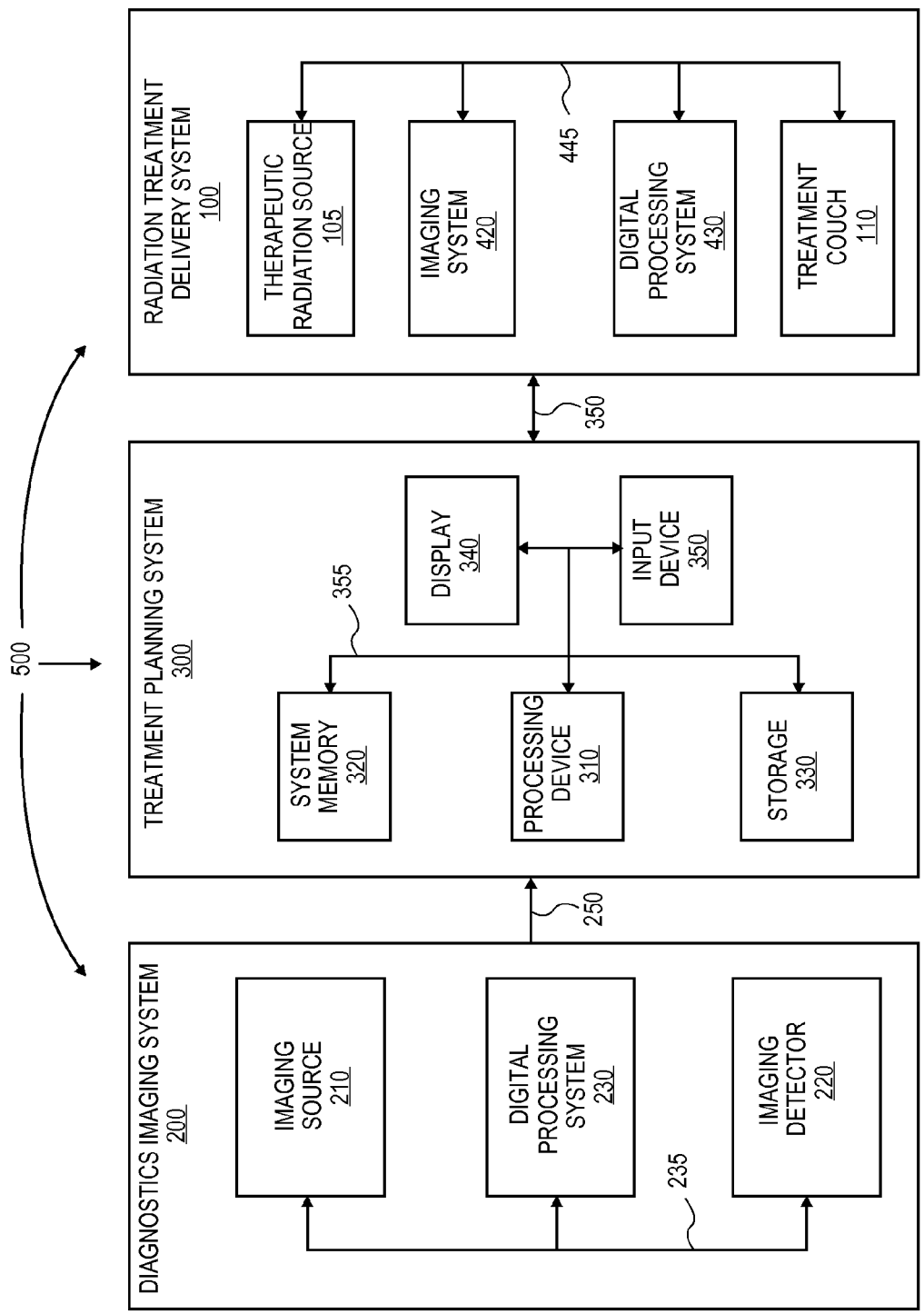
FIG. 2 is a block diagram showing the relationship of components of a radiation treatment delivery system in accordance with one embodiment of the invention.

FIG. 2 illustrates one embodiment of systems that may be used to perform radiation treatment in which features of the present invention may be implemented. As described below and illustrated in FIG. 2, system 500 may include a diagnostic imaging system 200, a treatment planning system 300, and a treatment delivery system 100. Diagnostic imaging system 200 may be any system capable of producing medical diagnostic images of a treatment region in a patient that may be used for subsequent medical diagnosis, treatment planning and/or treatment delivery. For example, diagnostic imaging system 200 may be a computed tomography (CT) system, a magnetic resonance imaging (MRI) system, a positron emission tomography (PET) system, an ultrasound system or the like. For ease of discussion, diagnostic imaging system 200 may be discussed below at times in relation to a CT x-ray imaging modality. However, other imaging modalities such as those above may also be used.

Diagnostic imaging system 200 includes an imaging source 210 to generate an imaging beam (e.g., x-rays, ultrasonic waves, radio frequency waves, etc.) and an imaging detector 220 to detect and receive the beam generated by imaging source 210, or a secondary beam or emission stimulated by the beam from the imaging source (e.g., in an MRI or PET scan). In one embodiment, diagnostic imaging system 200 may include two or more diagnostic x-ray sources and two or more corresponding imaging detectors. For example, two x-ray sources may be disposed around a patient to be imaged, fixed at an angular separation from each other (e.g., 90 degrees, 45 degrees, etc.) and aimed through the patient toward (an) imaging detector(s) which may be diametrically opposed to the x-ray sources. A single large imaging detector, or multiple imaging detectors, may also be used that would be illuminated by each x-ray imaging source. Alternatively, other numbers and configurations of imaging sources and imaging detectors may be used.

The imaging source 210 and the imaging detector 220 are coupled to a digital processing system 230 to control the imaging operation and process image data. Diagnostic imaging system 200 includes a bus or other means 235 for transferring data and commands among digital processing system 230, imaging source 210 and imaging detector 220. Digital processing system 230 may include one or more general-purpose processors (e.g., a microprocessor), special purpose processor such as a digital signal processor (DSP) or other type of device such as a controller or field programmable gate array (FPGA). Digital processing system 230 may also include other components (not shown) such as memory, storage devices, network adapters and the like. Digital processing system 230 may be configured to generate digital diagnostic images in a standard format, such as the DICOM (Digital Imaging and Communications in Medicine) format, for example. In other embodiments, digital processing system 230 may generate other standard or non-standard digital image formats. Digital processing system 230 may transmit diagnostic image files (e.g., the aforementioned DICOM formatted files) to treatment planning system 400 over a data link 250, which may be, for example, a direct link, a local area network (LAN) link or a wide area network (WAN) link such as the Internet. In addition, the information transferred between systems may either be pulled or pushed across the communication medium connecting the systems, such as in a remote diagnosis or treatment planning configuration. In remote diagnosis or treatment planning, a user may utilize embodiments of the present invention to diagnose or treatment plan despite the existence of a physical separation between the system user and the patient.

Treatment planning system 300 includes a processing device 310 to receive and process image data. Processing device 310 may represent one or more general-purpose processors (e.g., a microprocessor), special purpose processor such as a digital signal processor (DSP) or other type of device such as a controller or field programmable gate array (FPGA). Processing device 310 may be configured to execute instructions for performing the operations of the treatment planning system 300 discussed herein that, for example, may be loaded in processing device 310 from storage 330 and/or system memory 320.

Treatment planning system 300 may also include system memory 320 that may include a random access memory (RAM), or other dynamic storage devices, coupled to processing device 310 by bus 355, for storing information and instructions to be executed by processing device 310. System memory 320 also may be used for storing temporary variables or other intermediate information during execution of instructions by processing device 310. System memory 320 may also include a read only memory (ROM) and/or other static storage device coupled to bus 355 for storing static information and instructions for processing device 310.

Treatment planning system 300 may also include storage device 330, representing one or more storage devices (e.g., a magnetic disk drive or optical disk drive) coupled to bus 355 for storing information and instructions. Storage device 330 may be used for storing instructions for performing the treatment planning methods discussed herein.

Processing device 310 may also be coupled to a display device 340, such as a cathode ray tube (CRT) or liquid crystal display (LCD), for displaying information (e.g., a two-dimensional or three-dimensional representation of the VOI) to the user. An input device 350, such as a keyboard, may be coupled to processing device 310 for communicating information and/or command selections to processing device 310. One or more other user input devices (e.g., a mouse, a trackball or cursor direction keys) may also be used to communicate directional information, to select commands for processing device 310 and to control cursor movements on display 340.

It will be appreciated that treatment planning system 300 represents only one example of a treatment planning system, which may have many different configurations and architectures, which may include more components or fewer components than treatment planning system 300 and which may be employed with the present invention. For example, some systems often have multiple buses, such as a peripheral bus, a dedicated cache bus, etc. The treatment planning system 300 may also include MIRIT (Medical Image Review and Import Tool) to support DICOM import (so images can be fused and targets delineated on different systems and then imported into the treatment planning system for planning and dose calculations), expanded image fusion capabilities that allow the user to treatment plan and view dose distributions on any one of various imaging modalities (e.g., MRI, CT, PET, etc.). Treatment planning systems are known in the art; accordingly, a more detailed discussion is not provided.

Treatment planning system 300 may share its database (e.g., data stored in storage device 330) with a treatment delivery system, such as treatment delivery system 100, so that it may not be necessary to export from the treatment planning system prior to treatment delivery. Treatment planning system 300 may be linked to treatment delivery system 100 via a data link 350, which may be a direct link, a LAN link or a WAN link as discussed above with respect to data link 250. It should be noted that when data links 250 and 350 are implemented as LAN or WAN connections, any of diagnostic imaging system 200, treatment planning system 300 and/or treatment delivery system 100 may be in decentralized locations such that the systems may be physically remote from each other. Alternatively, any of diagnostic imaging system 200, treatment planning system 300 and/or treatment delivery system 100 may be integrated with each other in one or more systems.

Treatment delivery system 100 includes a therapeutic and/or surgical radiation source 105 to administer a prescribed radiation dose to a target volume in conformance with a treatment plan. Treatment delivery system 100 may also include an imaging system 420 to capture intra-treatment images of a patient volume (including the target volume) for registration or correlation with the diagnostic images described above in order to position the patient with respect to the radiation source. Treatment delivery system 100 may also include a digital processing system 430 to control radiation source 105, imaging system 420, and a patient support device such as a treatment couch 110. Digital processing system 430 may include one or more general-purpose processors (e.g., a microprocessor), special purpose processor such as a digital signal processor (DSP) or other type of device such as a controller or field programmable gate array (FPGA). Digital processing system 430 may also include other components (not shown) such as memory, storage devices, network adapters and the like. Digital processing system 430 may be coupled to radiation source 105, imaging system 420 and treatment couch 110 by a bus 445 or other type of control and communication interface.

Figure 3:
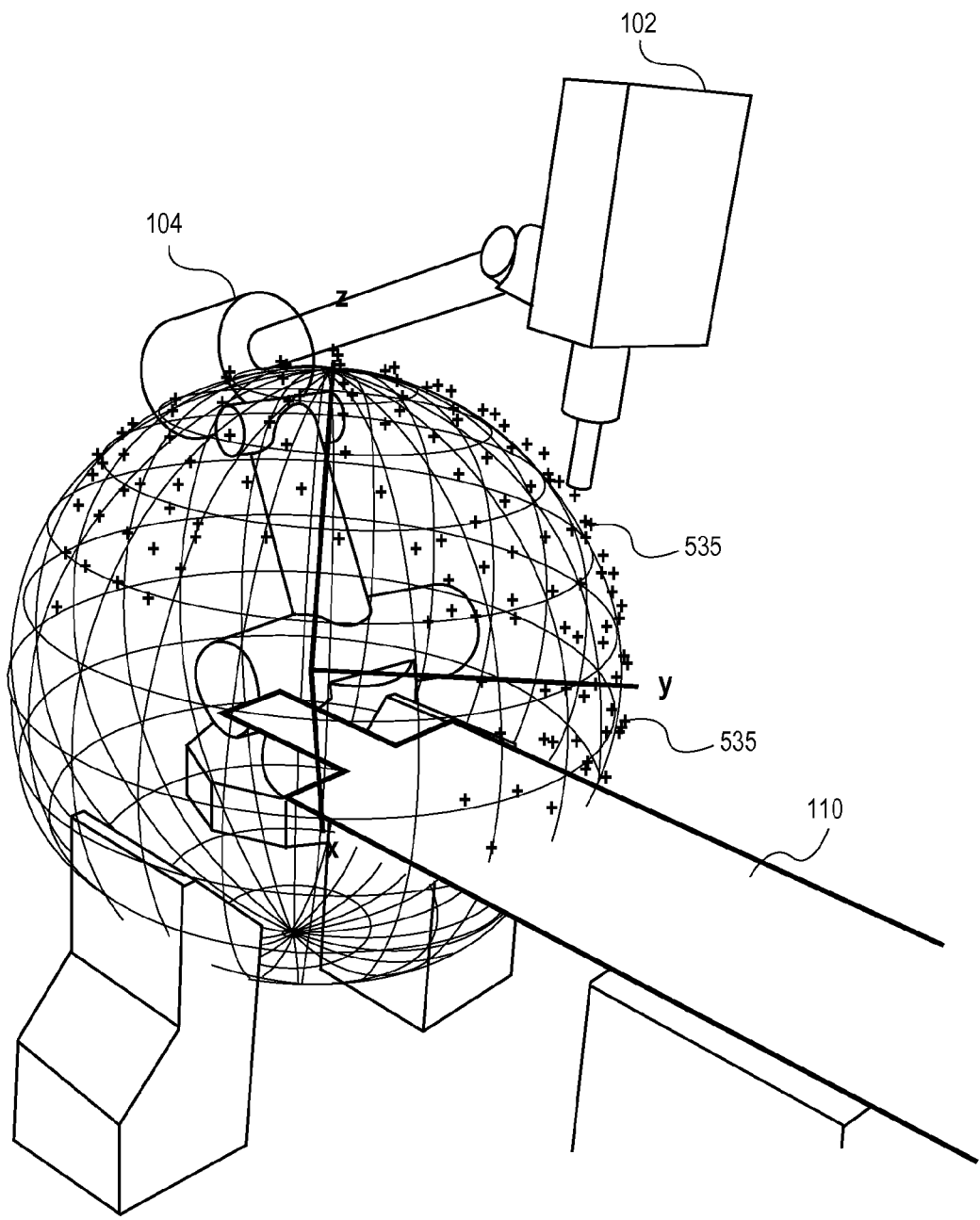
FIG. 3 is a perspective view of a workspace of a radiation treatment delivery system including a set of spatial nodes at which to position the radiation source, in accordance with one embodiment of the invention.

FIG. 3 illustrates positions where the radiation source 102 is allowed to stop and deliver a dose of radiation to the VOI within the patient. The spatial nodes 535, represented by the "+" symbol (only a few are illustrated), illustrate these positions. During delivery of a treatment plan, in one embodiment, a robotic arm 104 may be used to move radiation source 102 to each and every spatial node 535 following a predefined path. Alternatively, other types of mechanisms such as a gantry may be utilized to move radiation source 102. Even if a particular treatment plan does not call for delivery of a dose of radiation from a particular spatial node 535, radiation source 102 may still visit that particular spatial node 535. It should be appreciated that the complete node set may include more or fewer spatial nodes 535 than is illustrated or discussed.

Figure 4:
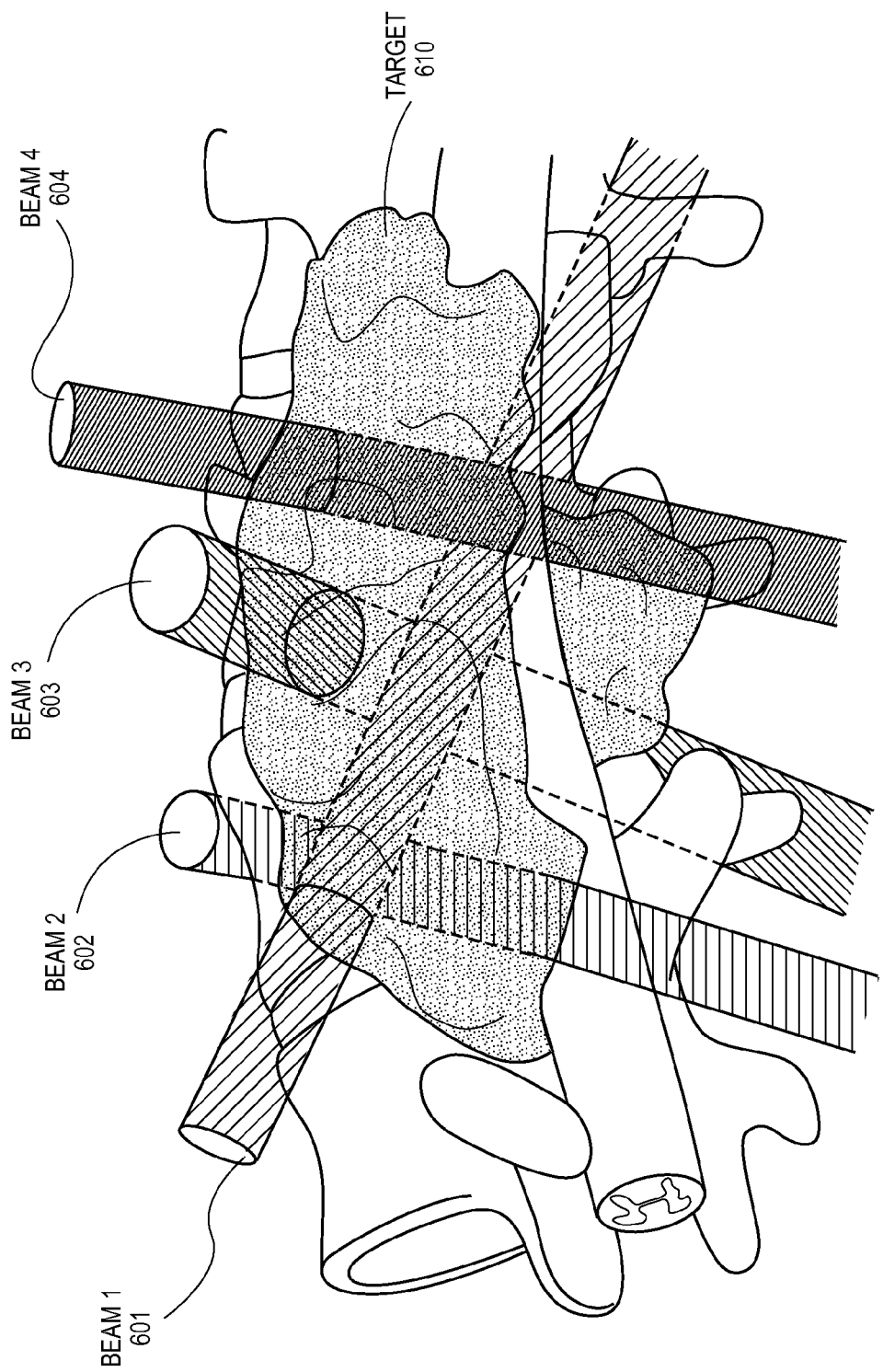
FIG. 4 is a schematic view of beam delivery in accordance with one embodiment of the invention.

Each node 535 may contribute multiple beam orientations to the treatment planning set of beams. In conformal planning, some radiation beams may or may not intersect or converge at a common point in three-dimensional space. In other words, the delivered radiation beams may be non-isocentric in that the beams do not necessarily converge on a single point, or isocenter, as illustrated in FIG. 4. The exemplary beams 601, 602, 603 and 604 intersect with target region 610, and possibly each other, but do not converge on a single point.

FIGS. 5A-H illustrate processes for tracking a cardiac target. Movement of a cardiac target includes a respiratory component and a cardiac pumping component. The respiratory component and the cardiac pumping components can be monitored and correlated to determine movement of the cardiac target. Radiation can then be delivered based on the movement of the cardiac target.

Figure 5A:
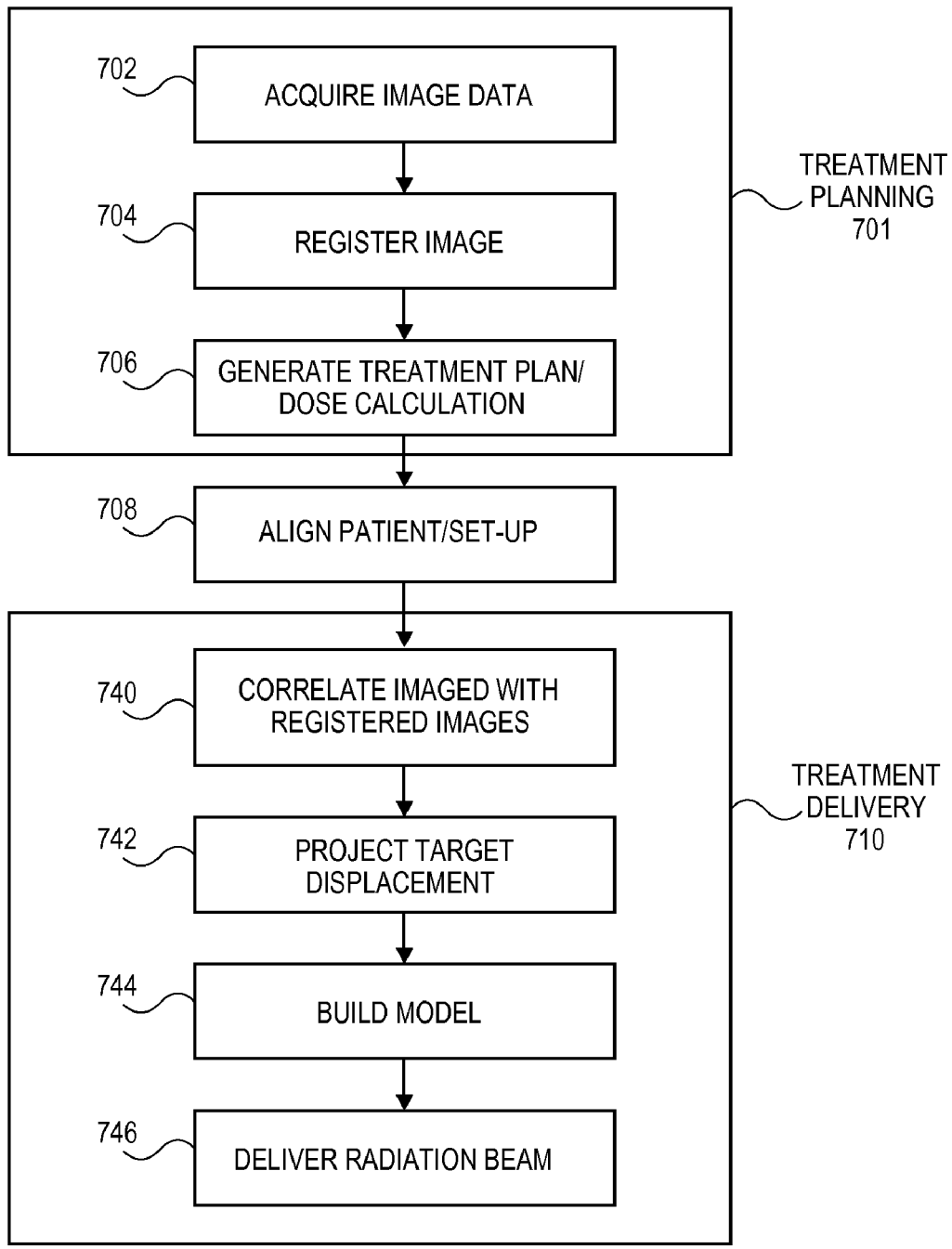
FIGS. 5A-H are block diagrams showing a method of cardiac target tracking in accordance with embodiments of the invention.

As shown in FIG. 5A, a process 700 for tracking a cardiac target typically begins with treatment planning (block 701). Treatment planning 701 begins by acquiring image data (block 702). In one embodiment, acquiring image data includes obtaining four-dimensional (4D) CT data of the target region and surrounding structures. The 4D CT scan data may be imported into a treatment planning system or may already reside on a diagnostic CT imaging system that is also used for treatment planning system that was used to perform the diagnostic 4D CT imaging.

Figure 6:
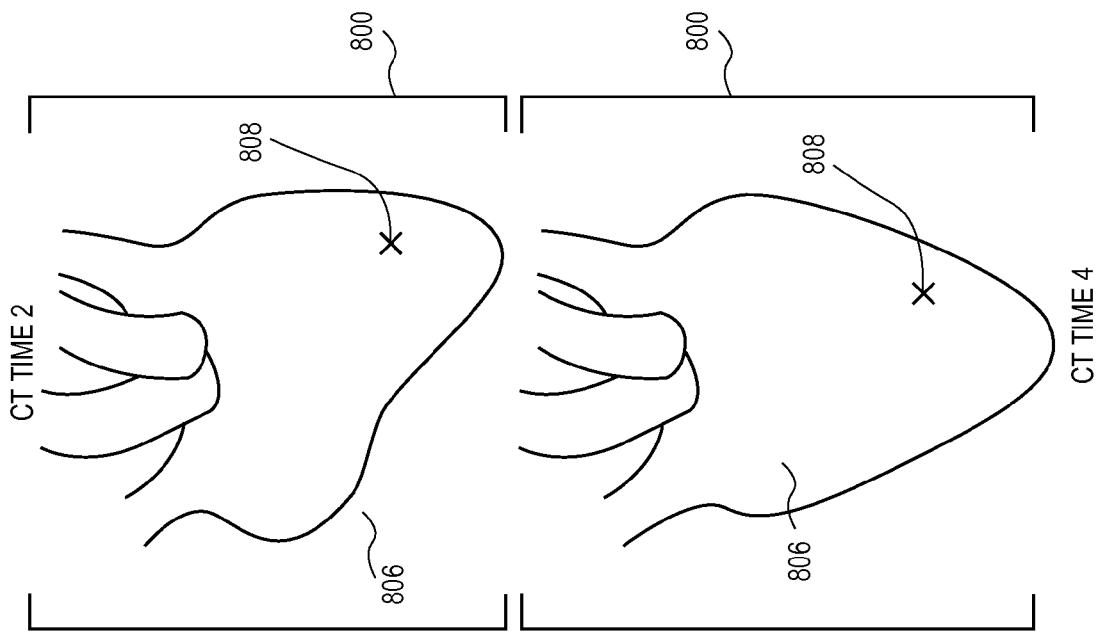
FIG. 6 is a schematic view of images from a 4D CT scan in accordance with one embodiment of the invention.
Figure 6:
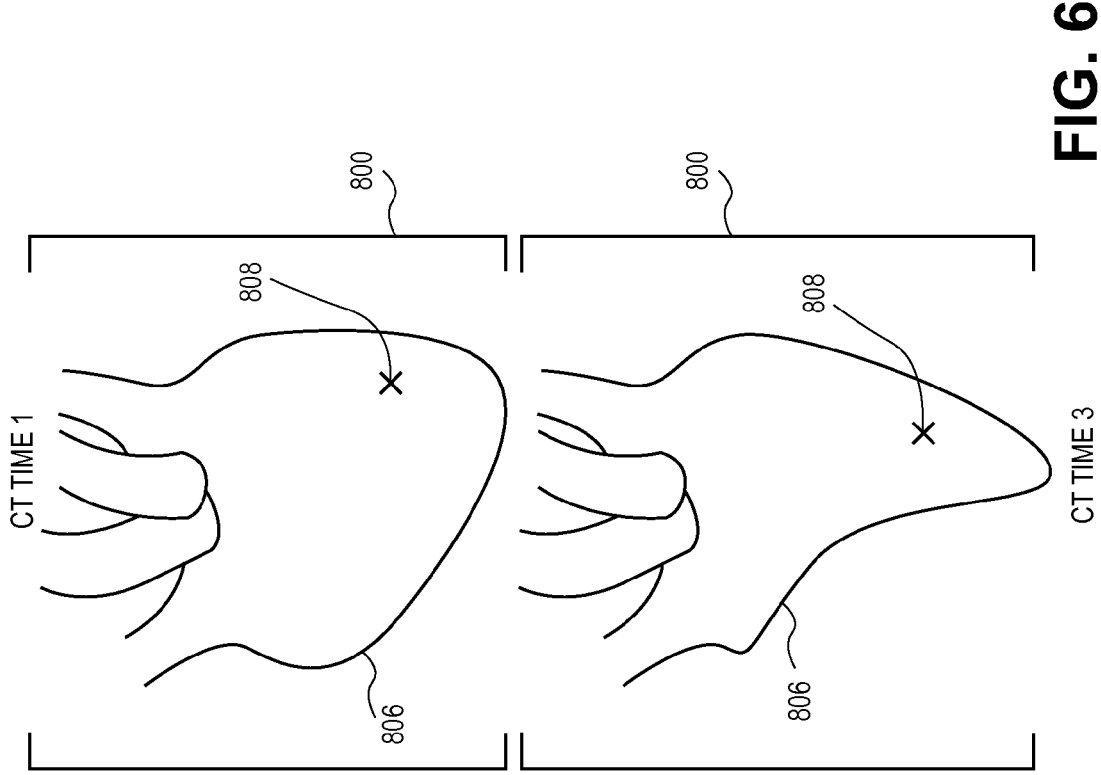

It should be noted that the four dimensions refer to three spatial dimensions and one temporal dimension, as opposed to four spatial dimensions. More specifically, the 4D CT scan data is a collection of three-dimensional (spatial) images, with each of the three-dimensional images taken at a different point in time in a motion cycle (e.g., during the respiratory cycle, cardiac cycle, artery pulsation, etc. of a patient) with a known temporal relationship. FIG. 6 is a conceptual illustration of a 4D CT scan of a patient's chest region including a cardiac target.

In one embodiment, the 4D CT scan data may be generated using a 4D CT scanner, for example, a 4D CT scanner produced by General Electric Corp. Alternatively, other 4D CT scanners may be used. A 4D CT scanner includes a device, such as a spirometer, strain gauge, optical tracker, etc., that is configured to take instantaneous measurements of the patient's position in the respiratory cycle. When a slice is acquired, the current respiratory measurement position and/or cardiac cycle position may be recorded. This measurement is used to place the CT slice in one of the 3D CT scans with the index closest to a given measurement of the respiratory cycle and/or cardiac cycle. The term 4D CT scan data is used herein to mean a set of two or more 3D images that represent different time points in a motion cycle regardless of the method of acquiring the scan data.

In one embodiment, the image data is acquired immediately after or during injection of contrast to highlight cardiac structures (e.g., atria and ventricles).

In some embodiments, the image data is a breath-hold 3D CT image, a cardiac-gated 4D CT image study or a respiratory-gated 4D CT image. A cardiac-gated 4D CT image study has 3D CT images at different phases in the cardiac cycle. A respiratory-gated 4D CT image study has 3D CT images at different phases in the respiratory cycle. In one embodiment, one image from the image study is selected as a reference for treatment planning. In some embodiments, the image selected is a breath hold 3D CT image or one of the images from a respiratory-gated 4D CT image to have a sufficient filed of view (FOV) for planning. It will be appreciated that other image data may be used, such as, for example, 3D MR or 4D MR, echocardiography image studies, or the like.

The process 700 continues by registering the image data (block 704). The registration may be rigid or non-rigid. In one embodiment, registration is performed and all scans are registered to a reference image to define respiratory and/or cardiac motion relative to a reference image coordinate system. In some embodiments, a cardiac motion model is computed during registration of the image data. In another embodiment, a respiratory motion model is generated from, for example, the respiratory-gated 4D CT image study. Scans are registered to the reference image to define the respiratory and/or cardiac motion relative to an image coordinate system of the reference image.

Figure 7:
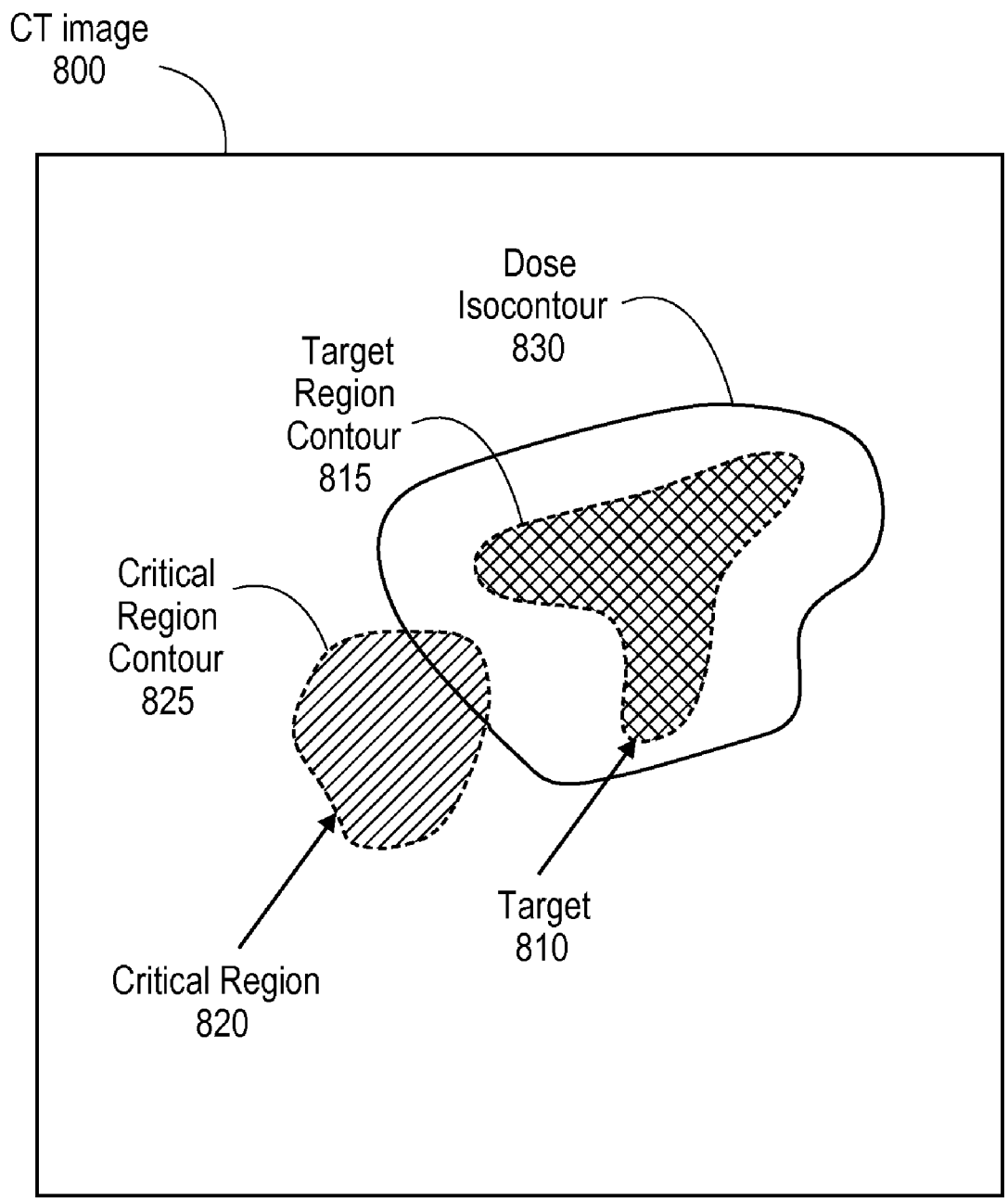
FIG. 7 is a schematic view illustrating a graphical output of a treatment planning software displaying a slice of a CT image in accordance with one embodiment of the invention.

During registration, the target region is delineated on a CT image, for example, as illustrated in FIG. 7 and discussed in more detail below. In one embodiment, one of the 4D CT images may be used for delineation of the target region and critical structures. Alternatively, delineation may be performed using a standard CT image. In yet another embodiment, delineation may be performed on an image of a different modality, for example, using magnetic resonance imaging (MRI.) Delineation can be defined in the reference image coordinate system. The target may be defined by manually defining a contour in each slice, by defining the contour in some slices and interpolating contours in intermediate slice, or by using automatic contour detection algorithms. In another embodiment, the target is defined in only the reference image.

Digitally Reconstructed Radiographs (DRRs) created from the CT image can be generated. For example DRRs can be generated for multiple phases of the cardiac and/or respiratory cycle. In another example, DRRs can be generated for different patient positions. In another example, DRRs can be generated for global patient positions combined with cardiac motion tracking. In one embodiment, the DRRs are generated based on a cardiac pumping frequency. It will be appreciated that the DRRs can be generated after a treatment plan is generated, during patient alignment or during treatment delivery, described in further detail hereinafter.

Next, a treatment plan is generated (block 706). The parameters necessary for treatment planning can be defined, such as, for example, dose constraints. The treatment plan is generated based on the treatment parameters. In one embodiment, the treatment plan is developed and optimized by enabling a planning algorithm that selects a set of treatment beam parameters to best satisfy the dose constraints. Once the target region and avoidance structures have been delineated, then the dose constraints may be applied to these structures. A user may define, for example, a minimum dose constraint for the target region and a maximum dose constraint for a critical region. A dose distribution is then calculated. Dose distribution techniques are well-known in the art; accordingly, a more detailed discussion is not provided. The generated treatment plan includes a set of radiation beam positions, orientations, collimator sizes and/or shapes, and beam durations. The beam on/off status can also be defined if the beam is to be gated based on different phases of the cardiac cycle and/or respiratory cycle. The treatment plan may include an optimization process that includes finding the beam parameters that best meets the specified objectives (i.e., dose constraints).

Although the method of the present invention is discussed above in regards to inverse, or conformal, planning, part or all of the treatment plan may be developed using forward planning techniques. In forward planning, the user of the treatment planning system (e.g., medical physicist) chooses the directions of the beams and the intensity of the beams and then the treatment planning algorithm calculates and displays the resulting dose distribution. More specifically, the user may specify particular directions and intensities for the radiation beams to be generated by the radiation treatment delivery system, choosing from a subset of available beams determined by constraints on the delivery system itself. The user may "guess" or assign, based on their experience, values to beam directions and intensities, or weights. The treatment planning system then calculates the resulting dose distribution. By evaluating the dose distribution, the user may manually change their selection of beams in an attempt to improve the dose distribution. The feedback given to the user is the dose profile corresponding to the current plan where beams may be removed, changed or added until the dose profile is deemed acceptable. After reviewing the resulting dose distribution, the user may adjust the values of the treatment parameters. The system re-calculates a new resulting dose distribution. This process may be repeated, until the user is satisfied by the resulting dose distribution, as compared to a desired distribution.

Once the dose has been calculated, it may be represented using a dose mask architecture. A dose mask is a representation where each beam has a mask: the mask elements each represent a distinct spatial position and the amount of dose per MU contributed by the beam at that position. In an exemplary embodiment, an inverse planning algorithm may be used that starts with approximately 1200 candidate beams. This set of beams may have on the order of 100 distinct points of origins, which may be referred to as nodes, which are discrete positions traversed by the radiation source that generates the beam during treatment.

An optimization step may be performed after the dose calculation. Various optimization algorithms such as an iterative algorithm and non-iterative algorithm may be used. With either an iterative algorithm or non-iterative (e.g., Simplex algorithm), a set of dose masks giving discretized estimates of dose/MU for each beam may be used as input. A set of dose constraints, input by the user to determine the desirable dose distribution for that planning task, may also be provided to the treatment planning algorithm. Optimization algorithms, such as an iterative algorithm and Simplex algorithm, are known in the art; accordingly, a more detail discussion is not provided.

In one embodiment, the cardiac and/or respiratory motion models can be used to calculate the dose distribution taking into account beam movement (e.g., dynamic alignment of the beam with the target, described in further detail hereinafter) and soft tissue deformation. In one embodiment, the dose distribution can be calculated after plan optimization on the reference image to show the effect of cardiac and/or respiratory motion on dose isocontours and treatment plan indices.

In another embodiment, the dose distribution can be calculated before optimization with the effect of motion being taken into account for the effect of motion during optimization.

With reference back to FIG. 5A, the process 700 continues by aligning a patient in the treatment delivery system (block 708). During patient alignment and/or treatment, real time x-ray images may be acquired. The image data may also be processed. In one embodiment, processing includes one or more of matching scale, bit-depth, intensity or other image parameters that would be appreciated by one of ordinary skill in the art. The processed x-ray image in each projection is independently registered against reference DRR images (from block 704), utilizing known registration methods. The patient position and/or the position of the radiation source can be corrected based on the registration results. It will be appreciated that the above process may be repeated during radiation treatment delivery to track and correct for patient movement. It will be appreciated that treatment planning can occur after patient alignment.

The process 700 continues with treatment delivery (block 710). Treatment delivery 710 includes correlating images acquired during delivery with the registered images (block 740). Target displacements are projected on the correlated images (block 742). A correlation model of the cardiac target movement can then be built (block 744). The treatment plan that is generated during the treatment planning process 701 is used to deliver radiation to the cardiac target (block 746).

Figure 5B:
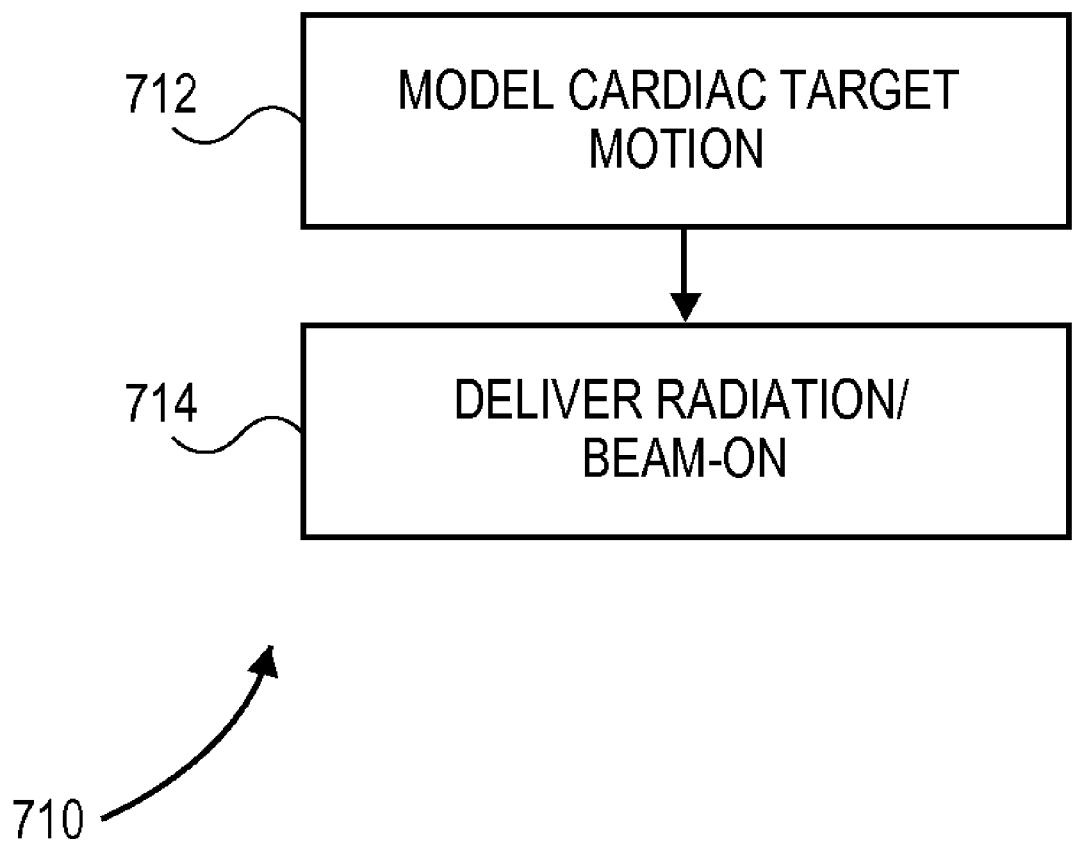

FIG. 5B illustrates treatment delivery 710 in further detail. In one embodiment, treatment delivery 710 is performed using the exemplary system of FIGS. 13A and 13B, described in further detail hereinafter. Treatment delivery 710 includes modeling a cardiac target movement 712. Cardiac target location is modeled by correlating the respiratory motion and cardiac pumping motion to determine the cardiac target motion with a correlation model. The correlation model receives data including imaging data, a cardiac pumping signal and a respiratory signal.

A plurality of diagnostic x-ray images of the cardiac area is obtained during treatment. The images are obtained continuously or near-continuously or can be gated to the cardiac pumping signal. The cardiac target region is registered to the corresponding region of the reference DRRs. In one embodiment, the cardiac target region is registered without fiducials. In another embodiment, the cardiac target region is registered fiducially. In one embodiment, the cardiac silhouette is matched with an x-ray image corresponding to the same structure in the DRR. The process determines the displacement of the cardiac target with respect to the reference frame defined during treatment planning. The cardiac silhouette is generally different in different phases of the cardiac cycle, and the position of the cardiac target within the cardiac silhouette is typically different during different phases. In one embodiment, one or more DRRs are generated for each x-ray image view for multiple phases in the cardiac cycle. In one embodiment, two or more DRRs are generated for different target positions or orientations relative to the imaging system for each of the multiple phases in the cardiac cycle. In one embodiment, the one or more DRRs are generated from the 3D CT images at different phases in the cardiac cycle. In one embodiment, the correlation model deforms a CT image to create individual 3D CT images at different phases in the cardiac cycle. The ECG signal can be used to index the individual images to derive DRRs at each phase in the cardiac cycle. The ECG signal can be used to pick a DRR to which the x-ray image is registered. Alternatively, the x-ray image can be registered to all DRRs to identify the best DRR. The cardiac target position is known in the CT coordinate space and is thus known in the DRR coordinate space. The matching of the cardiac silhouette in the x-ray image and DRR yields the 2D cardiac target position, which can be back projected to the CT images. Matching can be performed using x-rays acquired immediately after or during injection radiopaque contrast and DRRs generated from a CT image acquired immediately after or during injection of radiopaque contrast. Images can be acquired with and without contrast enhancement and subtracted at the same phase in the cardiac cycle, which can be accomplished by ECG gating.

Continuous or near-continuous signals representing cardiac pumping motion and/or respiratory motion are used to track the dynamic motion of the cardiac target. The x-ray image registration and the motion signals (respiratory and/or cardiac) are combined to form a correlation model. The correlation model defines the cardiac target motion in terms of the motion signals captured by the surrogated devices. $X_{target} = f_1(X_{dev1}) + f_2(X_{dev2}) + f_3(X_{dev3}) + \ldots f_n(X_{devn})$. For example, if an ECG signal and synchrony LED marker positions are used to determine the cardiac target motion, then the correlation model is $X_{target} = f_1(X_{ECG}) + f_2(X_{LED})$, assuming the respiratory motion and cardiac pumping motion are decoupled. In another example, the correlation model is $X_{target} = f(X_{ECG}, X_{LED})$.

In one embodiment, a respiratory correlation model is built, and a cardiac pumping motion is superimposed on the respiratory correlation model. For example, the cardiac target position is computed for each x-ray image and the registration process computes the cardiac target position using the cardiac pumping signal to pick the cardiac cycle phase and corresponding DRR. The set of cardiac target positions can be used to generate a respiratory correlation model by correlating the cardiac target positions with the respiratory signal. In one embodiment, the model averages out the cardiac pumping motion if the cardiac pumping motion is small relative to the respiratory motion. For example, if the target is in the left atrium, the model may average out the cardiac pumping motion. In another embodiment, the cardiac target is adjusted to a reference position in the cardiac cycle. For example, for each phase in the cardiac cycle, the cardiac position can be computed relative to its position in a reference phase of the cardiac cycle. The cardiac target position offset can be applied to the measured cardiac position at the time an x-ray image is acquired. The resulting adjusted cardiac target position is where the cardiac target position would be if the heart was at the reference phase in the cardiac cycle and thus represents only the effect of respiration on cardiac position. The adjusted cardiac position can be used to generate a respiratory correlation model by correlating the adjusted cardiac target positions with the respiratory signal.

Treatment delivery 710 continues by delivering radiation to the cardiac target 712. During treatment, x-ray images can be obtained continuously, as described above. The mathematical correlation model can be verified with the acquired data periodically or continuously. Similarly, the actual cardiac target position can be compared with a predicted cardiac target position. The correlation model can be adapted to changes in cardiac target position and motion to adjust the treatment delivery in real-time.

In one embodiment, the radiation source is moved to track the cardiac target movement, including both the respiratory motion and the cardiac pumping motion. In another embodiment, the radiation source is moved to track only the respiratory motion. In some embodiments, radiation delivery is gated. It will be appreciated that the radiation source can be moved to track the respiratory motion and, optionally, the cardiac motion when the radiation delivery is gated.

It will be appreciated that several variations of modeling and radiation delivery can be used to track and treat cardiac targets, as explained in further detail with reference to Table 1 and FIGS. 5C-5H. The term $\phi_c$ represents the phase of the cardiac cycle. The term C represents the cardiac motion, and the term R represents the respiratory motion.

TABLE 1

Cardiac Target Tracking

| Treatment Planning | Model | Treatment Delivery Beam-On |
|---|---|---|
| Make DRR($\phi$c), XT($\phi$c) | C + R | C + R |
| Make DRR($\phi$c), XT($\phi$c) | C + R | $C_{gated}$ + R |
| Make DRR($\phi$c), XT($\phi$c) | $C_{gated}$ + R | $C_{gated}$ + R |
| Make DRR($\phi$c), XT($\phi$c) | $C_{gated}$ + R | R |
| Make DRR($\phi$c), XT($\phi$c) | C + R | R |
| Compute Cardiac Motion f($\phi$c), XT($\phi$c) | Interpolation: R + $C_{planning}$ | C + R |
| Compute Cardiac Motion f($\phi$c), XT($\phi$c) | Correction: R + $C_{planning}$ | C + R |

Figure 5C:
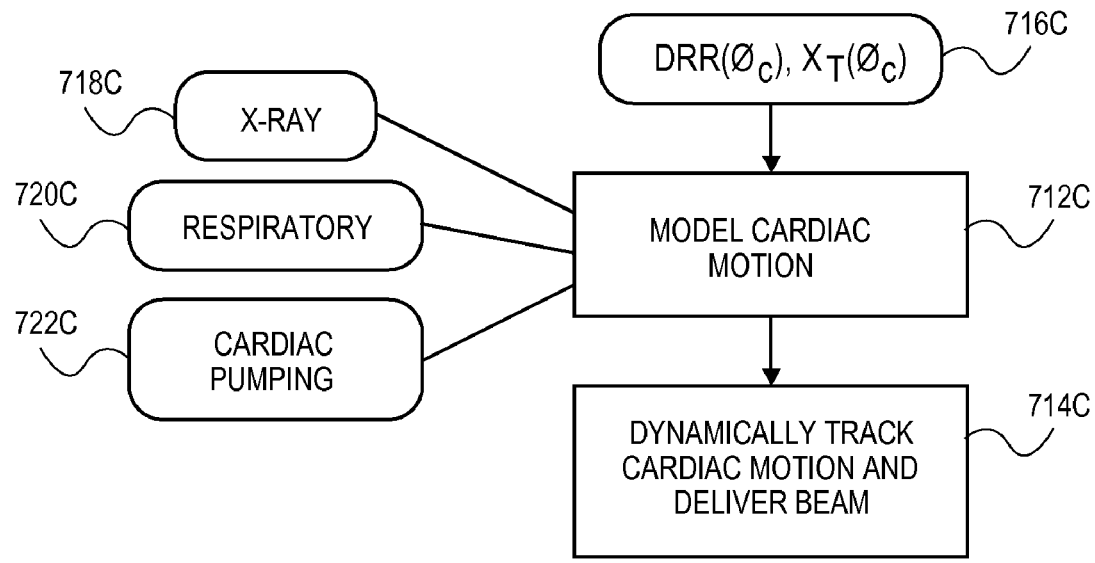

As shown in FIG. 5C, cardiac motion is modeled at block 712c. The model is a correlation model of cardiac target position as a function of both input signals: respiratory motion 720c and cardiac pumping motion 722c. The model also receives x-ray images of the target 718c. In the embodiment illustrated in FIG. 5C, the x-ray image acquisition is at a high enough frequency to follow the cardiac motion. The model also receives the treatment planning data (DRR($\phi_c$), $X_T(\phi_c)$) 716c). As described above, the model identifies the cardiac target location during treatment. The treatment delivery system can then dynamically track cardiac motion and deliver the radiation beam 714c. The treatment delivery system moves the source to follow the respiratory component and the cardiac components. The treatment delivery system can move or shape the beam sufficiently to track the cardiac target motion. The beam can be moved dynamically with the moving cardiac target, as determined by the model.

In one embodiment, the beam is shaped with dynamic collimation based on the cardiac pumping motion. In another embodiment, a fixed collimator is rocked or gimbaled based on the cardiac pumping motion. In still another embodiment, the beam is bent with electromagnetic steering.

It will be appreciated that treatment planning 701 can take into account that dynamic tracking will be used during delivery. For example, the dose can be calculated in the 4D treatment planning step assuming the beam is aligned with the target continuously during cardiac pumping and respiratory motion.

Figure 5D:
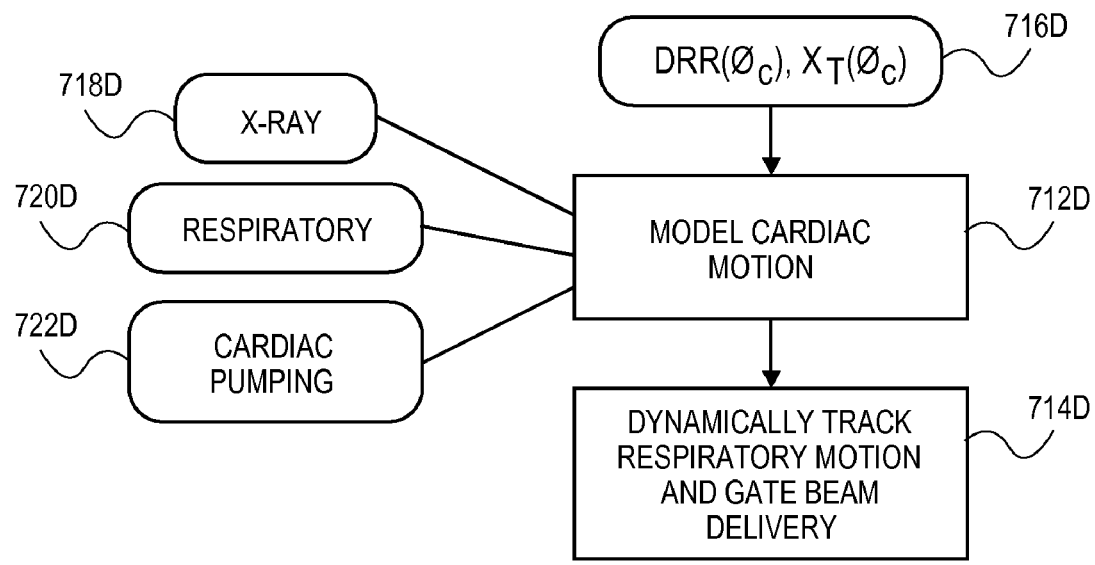
Figure 14:
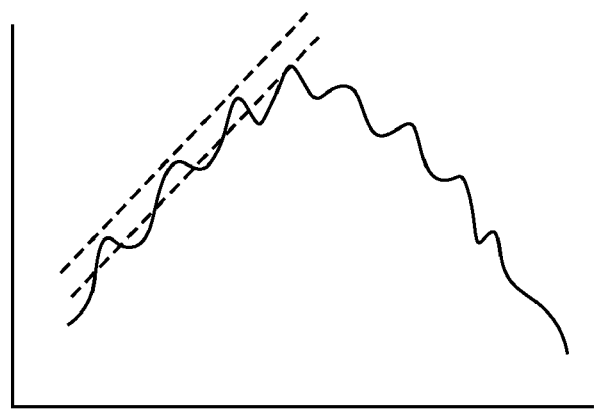
FIG. 14 is a schematic view illustrating gated delivery of radiation treatment in accordance with one embodiment of the invention.

FIG. 5D illustrates a treatment delivery process 510 in which the beam is gated. A model is generated (712d) using the x-ray input 718d, respiratory motion input 720d, cardiac pumping input 722d and treatment planning data (DRR($\phi_c$), $X_T(\phi_c)$) 716d). Radiation is delivered by dynamically moving the radiation source to track the respiratory motion and beam delivery is gated 714d. In one embodiment, the beam is turned on when the cardiac target is sufficiently close to the beam. In one embodiment, the beam is turned on based on a reference phase of the cardiac cycle. FIG. 14 graphically illustrates the process of FIG. 5D.

It will be appreciated that beam gating may be taken into account during treatment planning as well. For example, the dose can be calculated in the 4D treatment planning step assuming the beam is aligned with the target continuously during the respiratory motion with the heart at a fixed phase in the cardiac cycle.

Figure 5E:
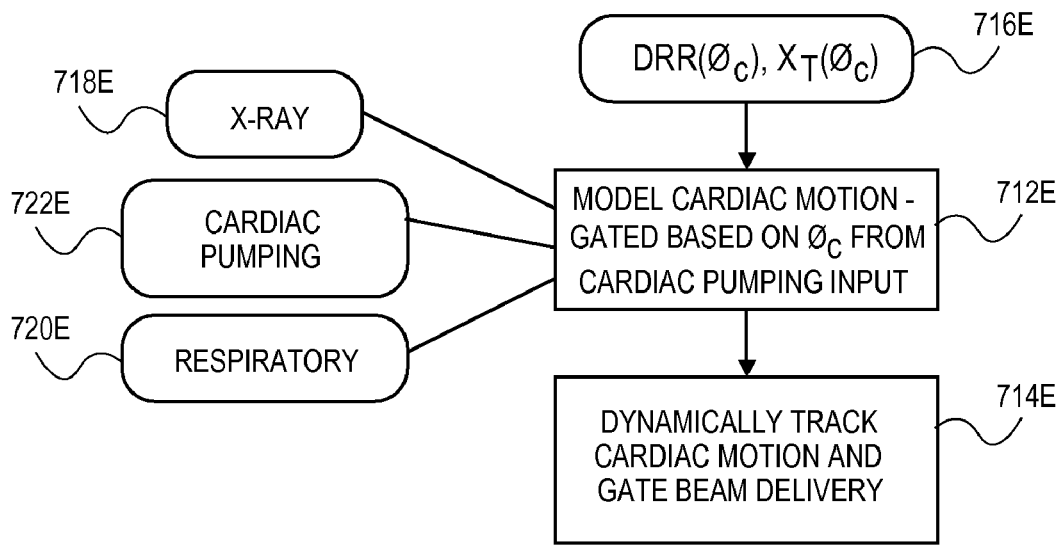
Figure 15:
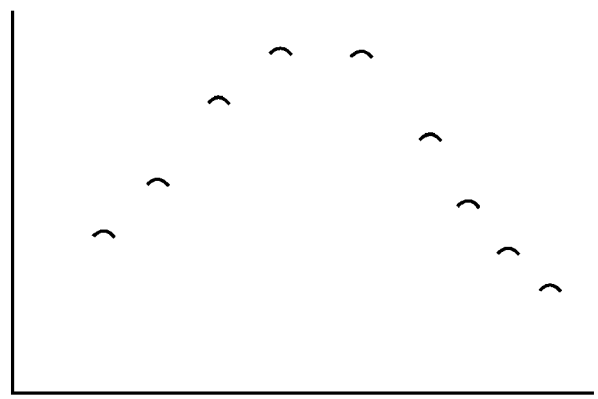
FIG. 15 is a schematic view illustrating gated acquisition and gated delivery of radiation treatment in accordance with one embodiment of the invention.

FIG. 5E illustrates a treatment process 710 in which the model uses gated image acquisition. A model is generated (712e) using the x-ray input 718e, respiratory motion input 720e, cardiac pumping input 722e and treatment planning data (DRR($\phi_c$), $X_T(\phi_c)$) 716e). In the embodiment of FIG. 5E, the x-ray input 718e is acquired at reference phases in the cardiac cycle using the cardiac pumping input 722e. For example, an ECG signal may trigger acquisition of the x-ray images used by the model. Thus, in the embodiment of FIG. 5E, the cardiac motion model is the respiratory motion model with the cardiac cycle motion computed from 4D imaging superimposed on the respiratory motion model. The treatment delivery system can then dynamically track cardiac motion and deliver the radiation beam 714e. FIG. 15 graphically illustrates the process of FIG. 5E. In one embodiment, the radiation is delivered by dynamically moving the radiation source to track the respiratory motion and beam delivery is gated. In another embodiment, the radiation is delivered by dynamically moving the radiation source to only track the respiratory motion, and the beam delivery is not gated, even though the model uses the gated cardiac motion. Using the gated cardiac motion for the model may simplify modeling the motion, but the beam delivery may not use the gated cardiac motion because the gating may take too long.

Figure 5F:
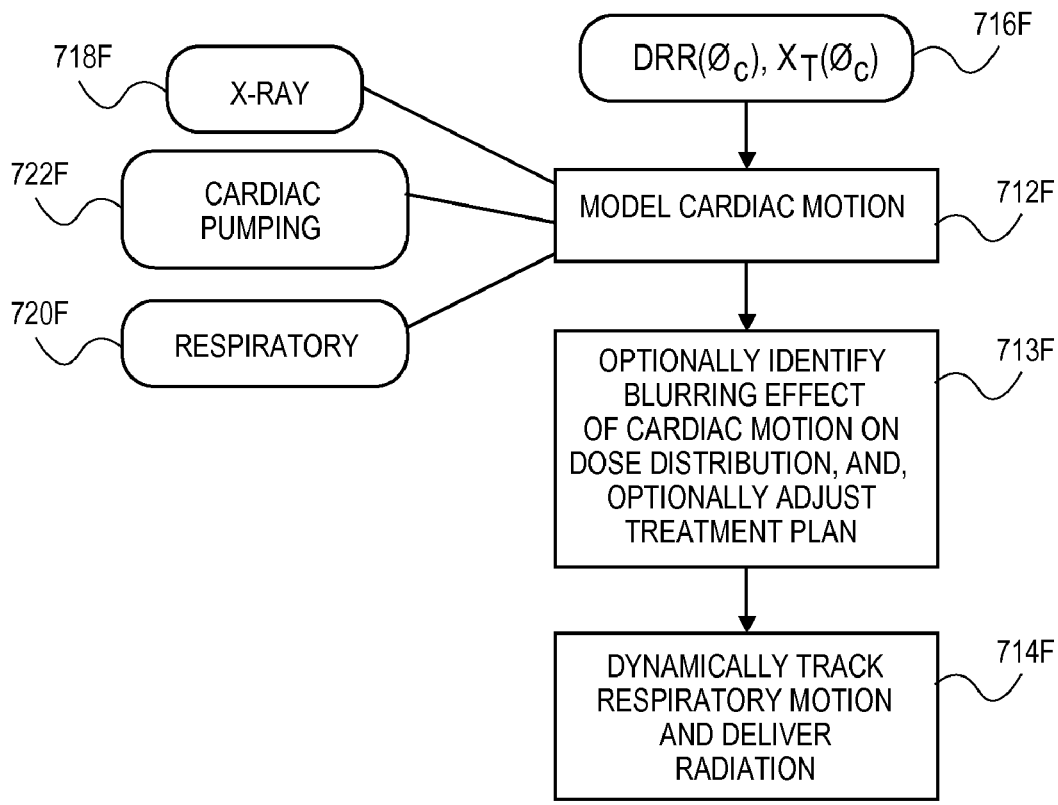
Figure 16:
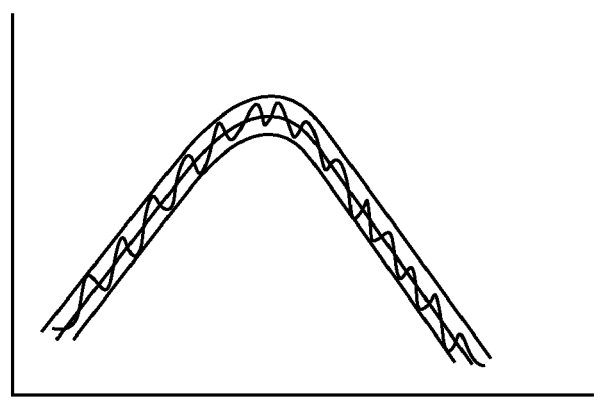
FIG. 16 is a schematic view illustrating a blurring effect of cardiac motion in accordance with one embodiment of the invention.

FIG. 5F illustrates a process in which a blurring effect on dose distribution resulting from the cardiac target motion is examined. A model is generated (712f) using the x-ray input 718f, respiratory motion input 720f, cardiac pumping input 722f and treatment planning data (DRR($\phi_c$), $X_T(\phi_c)$) 716f). In one embodiment, a full model is developed as described above with reference to FIGS. 5C and 5D. In another embodiment, a gated model is developed as described above with reference to FIG. 5E. The model may be used to optionally identify the blurring effect of cardiac motion on the dose distribution, and, optionally, the treatment plan can be adjusted 713f. FIG. 16 graphically illustrates the blurring effect. The treatment delivery system can then deliver the radiation beam 714f. In one embodiment, the treatment delivery system tracks only the respiratory motion.

Figure 5G:
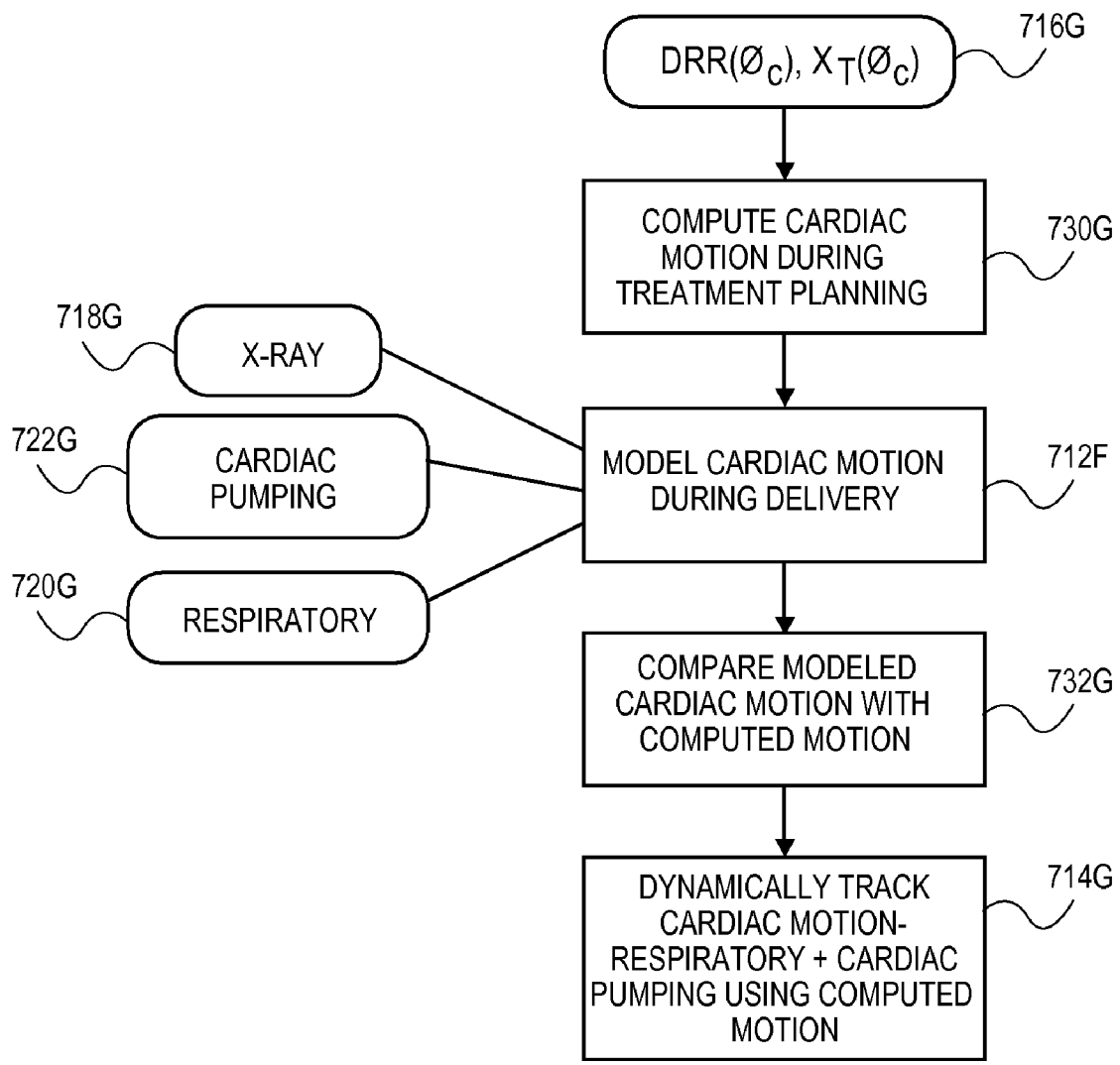
Figure 5H:
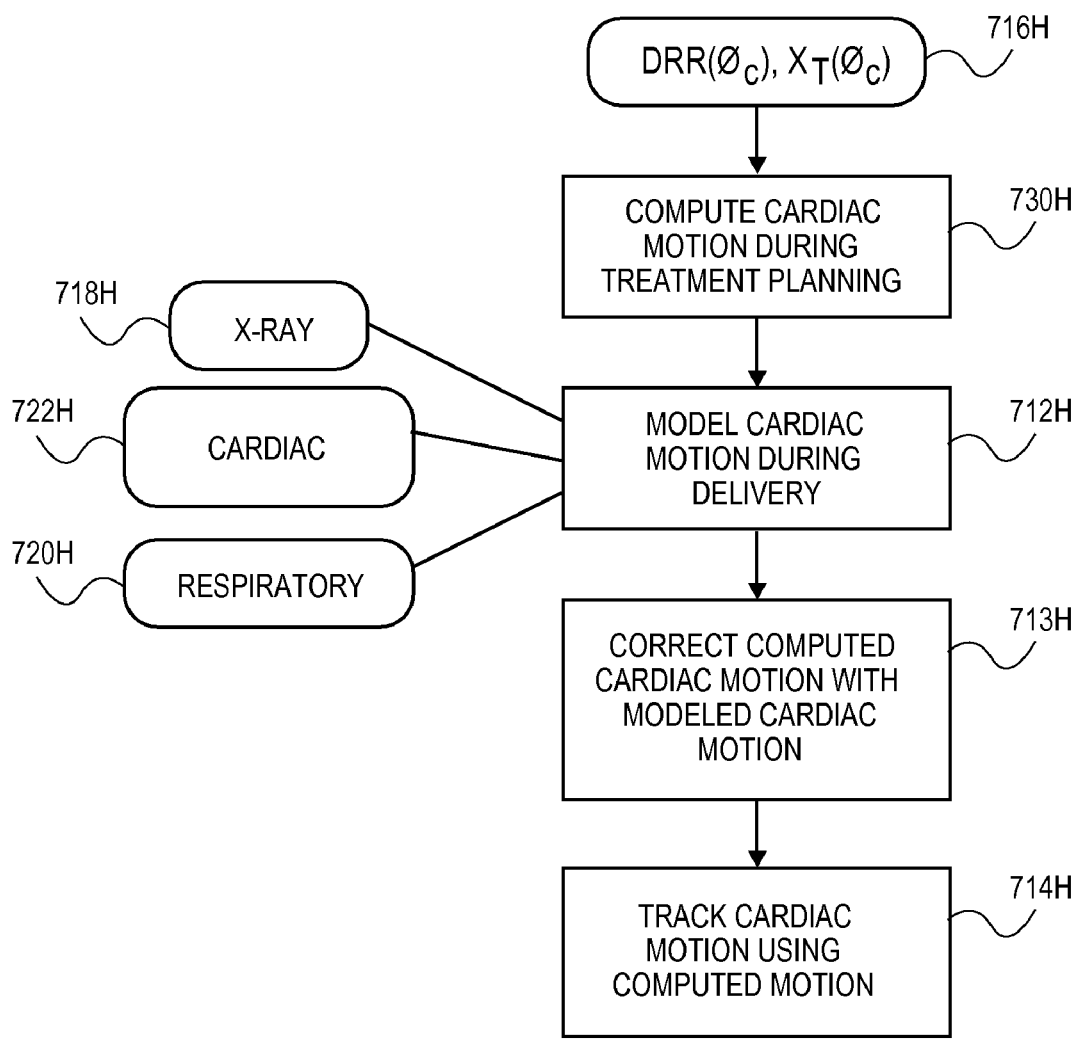

In some embodiments, the cardiac cycle motion is computed during treatment planning using an ECG signal (or other cardiac motion input), as shown in FIGS. 5G and 5H. In FIGS. 5G and 5H, before a model is generated (712g, h) using the x-ray input 718g, h, respiratory motion input 720g, h, cardiac pumping input 722g, h and treatment planning data (DRR($\phi_c$), $X_T(\phi_c)$) 716g, h), cardiac motion is computed during treatment planning 730g, h. In one embodiment, the treatment planning image acquisition is acquired with gating based on a cardiac pumping motion. For example, an ECG signal can trigger 4D CT image acquisition corresponding to one or more reference phases in a cardiac cycle. In FIG. 5G, the model is compared with the computed motion 732g so the radiation can be delivered based on the computed motion 714g. In FIG. 5H, the computed motion is corrected using the model 732h before the radiation is delivered based on the computed motion 714h.

FIG. 6 is a conceptual illustration of a graphical output of a treatment planning system displaying a slice of a CT image in which delineation may be performed. The exemplary 4D CT scan 800 of FIG. 6 includes four 3D CTs taken a four time points: CT Time 1, CT Time 2, CT Time 3 and CT Time 4. The illustration of the CT image 800 includes a target (e.g., pathological anatomy such as a tumor, lesion, vascular malformation, etc.) 808 in a heart 806 that is targeted for treatment. The CT image may also include a critical region 810 that is positioned near the target region 808, as shown in FIG. 7. The treatment planning software enables the generation of a critical region contour 812 around the critical region 810 and a target region contour 814 around the target region 808. A user manually delineates points (e.g., some of the dots on the contour lines of FIG. 7) on the display that are used by the treatment planning software to generate the corresponding contours. Based on specified minimum dose to the target region 808 and the maximum dose to the critical region 810, the treatment planning software generates the dose isocontour 814 for the target region 808. The dose isocontour 814 represents a given dose percentage (e.g., 60%, 70%, 80%, etc.) of a specified prescription dose for the target region 808. Ideally, the dose isocontour 814 should perfectly match the contour of the target region 808. However, in some cases, the dose isocontour 814 generated by the treatment planning software is not optimal, and can include portions of the critical region 810, as illustrated in FIG. 7.

Figure 8:
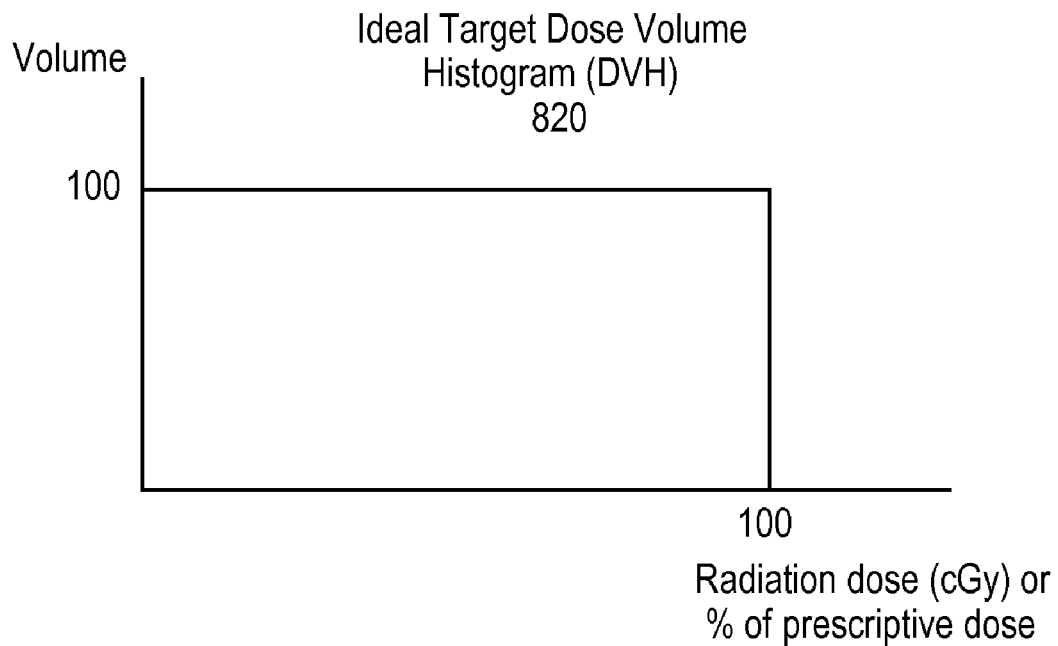
FIG. 8 is a graph illustrating an ideal DVH for a pathological anatomy in accordance with one embodiment of the invention.
Figure 9:
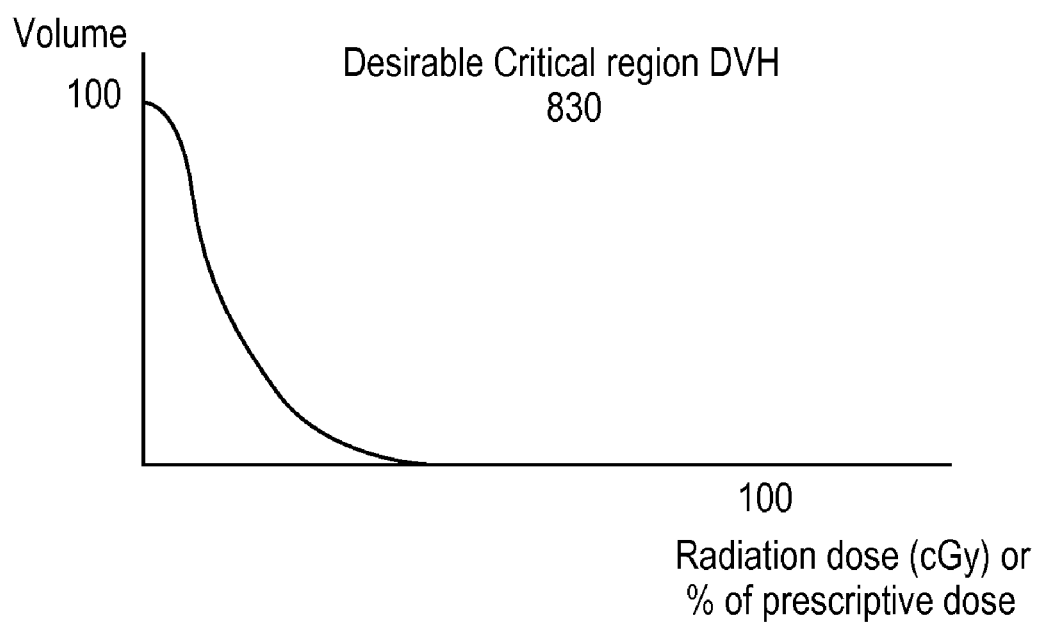
FIG. 9 is a graph illustrating a desirable DVH for a critical region in accordance with one embodiment of the invention.

The two principal requirements for an effective radiation treatment system are homogeneity and conformality. Homogeneity is the uniformity of the radiation dose over the volume of the target region characterized by a dose volume histogram (DVH). An ideal DVH 820 for the target region 808 would be a rectangular function as illustrated in FIG. 8, where the dose is 100 percent of the prescribed dose over the volume of the target region 808. In an ideal case, the dose would also be zero elsewhere. A desirable DVH 830 for a critical region 810 would have the profile illustrated in FIG. 9, where the volume of the critical structures receives as little of the prescribed dose as possible. Conformality is the degree to which the radiation dose matches (conforms to) the shape and extent of the target region (e.g., tumor) in order to avoid damage to critical adjacent structures. More specifically, conformality with respect to a target region VOI is a measure of the amount of the region receiving the prescription (Rx) dose or more, that is contained within the VOI. Conformality may be measured using a conformality index (CI)=(total volume at>=Rx dose)/(target volume at>=Rx dose). Perfect conformality results in a CI=1. With conventional radiotherapy treatment, using treatment planning software, a clinician identifies a dose isocontour for a corresponding VOI for application of a treatment dose (e.g., 3000 cGy).

Figure 10:
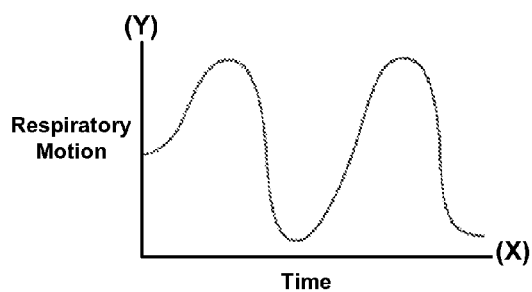
FIG. 10 is a schematic view of respiratory data in accordance with one embodiment of the invention.
Figure 11:
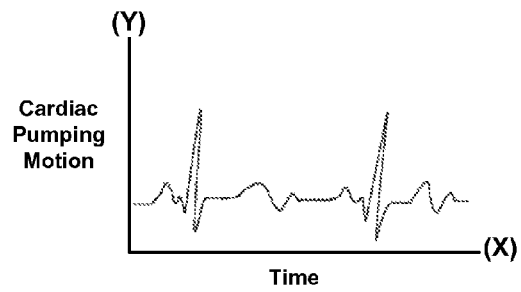
FIG. 11 is a schematic view of ECG data in accordance with one embodiment of the invention.
Figure 12:
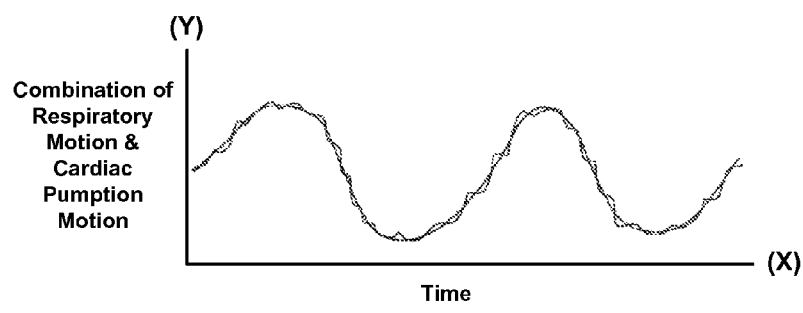
FIG. 12 is a schematic view of cardiac target moving illustrating respiratory motion and cardiac motion in accordance with one embodiment of the invention.

FIG. 10 graphically illustrates respiratory motion for a patient. The peaks correspond to exhalation and the valleys correspond to inhalation. FIG. 11 graphically illustrates an ECG signal. The ECG signal for a typical cardiac cycle includes a P wave, QRS complex and a T wave, separated by segments. The P wave, QRS complex, T wave, and various segments can be used as reference points for tracking cardiac target movement or may be used to calculate the movement of the target based on cardiac pumping. FIG. 12 illustrates an exemplary target movement taking into account a combination of respiratory motion and cardiac pumping motion. As illustrated in FIG. 12, the cardiac pumping motion frequency tends to be about five to ten times greater than the respiratory motion frequency.

Figure 13A:
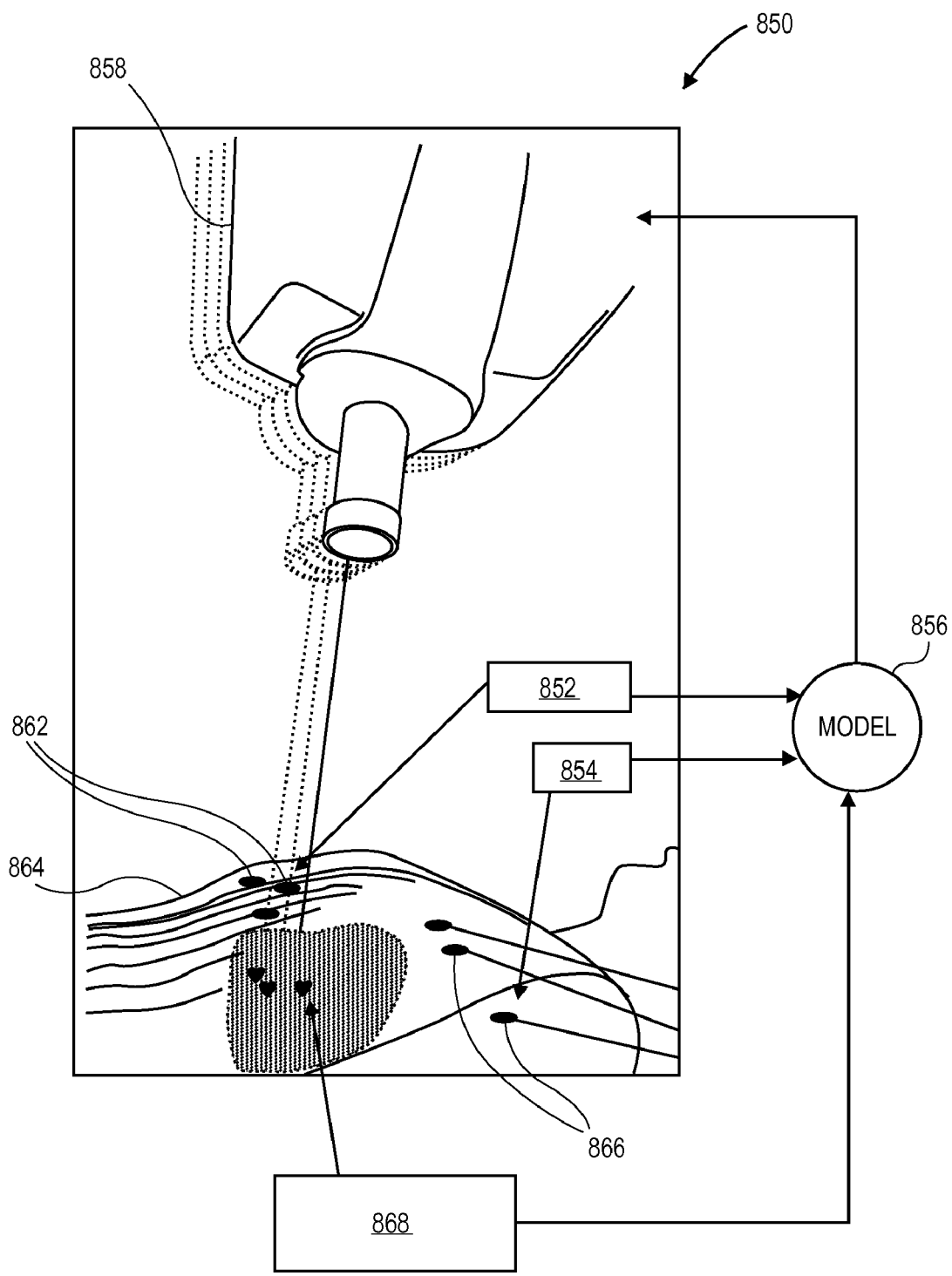
FIGS. 13A and 13B are schematic views of a system for cardiac target tracking in accordance with one embodiment of the invention.

FIG. 13A shows a schematic view of a system for cardiac target tracking in accordance with one embodiment of the invention. The illustrated system 850 includes a respiratory input 852, a cardiac input 854, a model 856 and a radiation source 858. In one embodiment, the radiation source 858 is the radiation source 102 of FIG. 1. The model 858 may be implemented on one or more of the systems described above with reference to FIG. 2. It will be appreciated that the model may also be implemented as a separate system that is in communication with the systems of FIG. 2.

The respiratory input 852 may include one or more external markers 862 that are secured to the exterior 864 of the patient in order to monitor the patient's breathing cycle (i.e., respiratory motion). In one embodiment, the external marker 862 may be a device such as a light source or a metal button attached to a vest worn by the patient. Alternatively, the external marker 862 may be attached to the patient's clothes or skin in another manner. In another embodiment, other types of external or internal markers may be used instead of or in addition to the illustrated external marker 862. The SYNCHRONY® system, developed by Accuray Incorporated, is one example of such a tracking system. Alternatively, other tracking systems can be used.

In addition, the cardiac pumping input 854 may include one or more ECG leads 866 that are placed on the patient's exterior to monitor the cardiac pumping frequency of the heart.

The data from the external markers 862 and the ECG leads 866 are sent to the model 856. The model 856 can use the respiratory motion and/or cardiac pumping motion, as described above, to track a cardiac target location 868. The model 856 may be a computer system. In one embodiment, the model 856 is integrated with one or more of the systems described above with reference to FIG. 2.

Figure 13B:
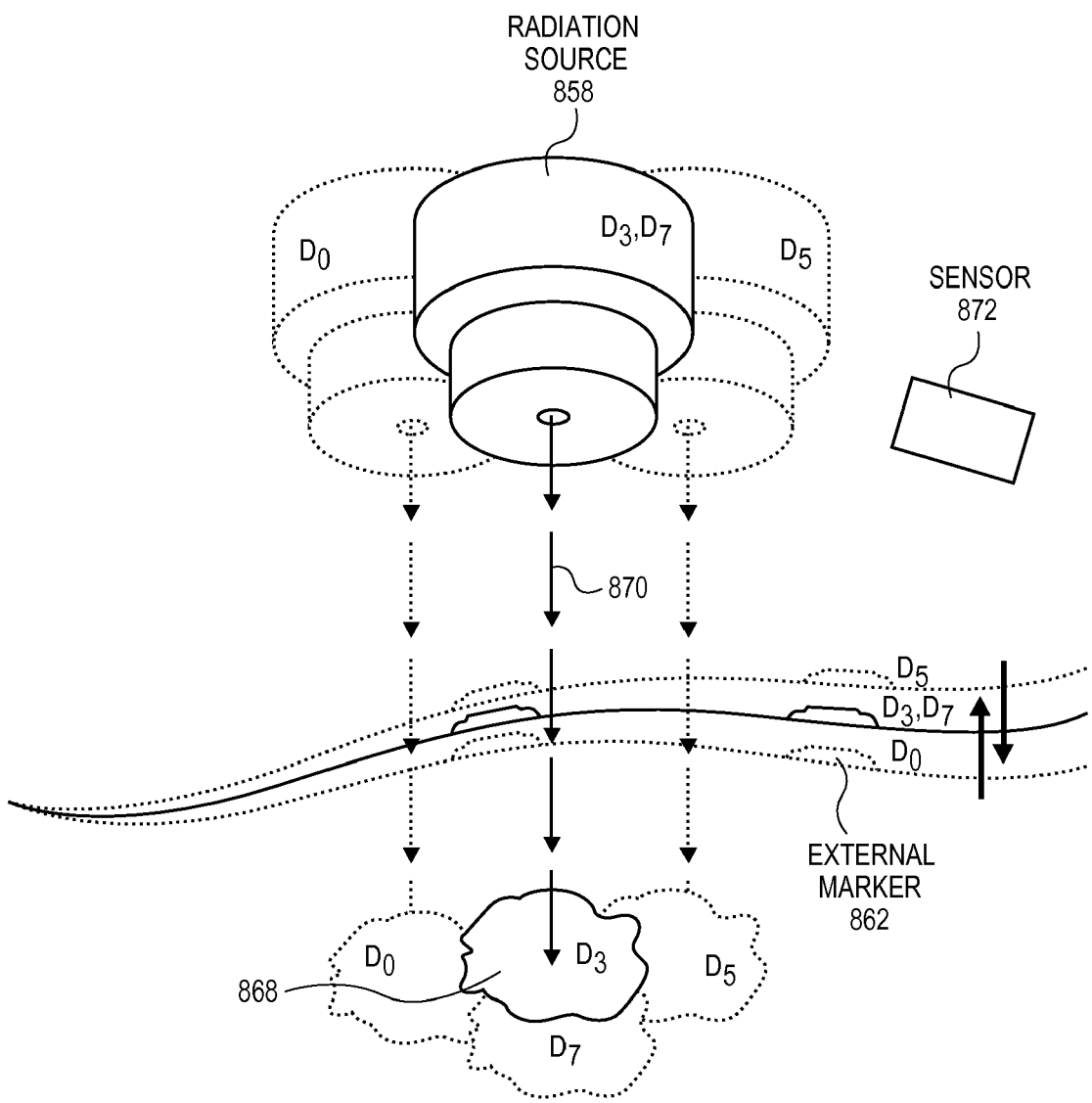

FIG. 13B illustrates a schematic view of treatment tracking using the system of FIG. 13A in accordance with one embodiment of the invention. In one embodiment, the radiation source 858 moves in one or more dimensions to position and orient itself to deliver a radiation beam 870 to the target 868. The radiation source 858 tracks the movement of the target 868. A tracking sensor 872 tracks the location of the external marker 862. For example, the tracking sensor 872 may track upward movement of the external marker 862 during an inspiration interval and downward movement of the external marker 862 during an expiration interval. It will be appreciated that the cardiac pumping motion can also be tracked.

As one example, the depicted target 868 is shown in four positions designated as D1, D3, D5, and D7. Similarly, the external marker 862 is shown in a first position, D1, a second position, D3, a third position, D5, and a fourth position, D7, which correspond to the positions of the target 868. By correlating the positions of the external marker 862 and the cardiac pumping input 854 to the target 868, the position of the target 868 may be derived. The radiation source 858 is also shown in a first position, D1, a second position, D3, a third position, D5, and a fourth position, D7, which also correspond to the positions of the target 868. In this way, the movements of the radiation source 858 may be substantially synchronized to the movements of the target 868.

FIG. 14 graphically illustrates gated delivery of radiation using the cardiac target location. FIG. 15 graphically illustrates gated acquisition and delivery of radiation using the cardiac target location. FIG. 16 graphically illustrates the blurring effect of the cardiac target location.

Figure 17:
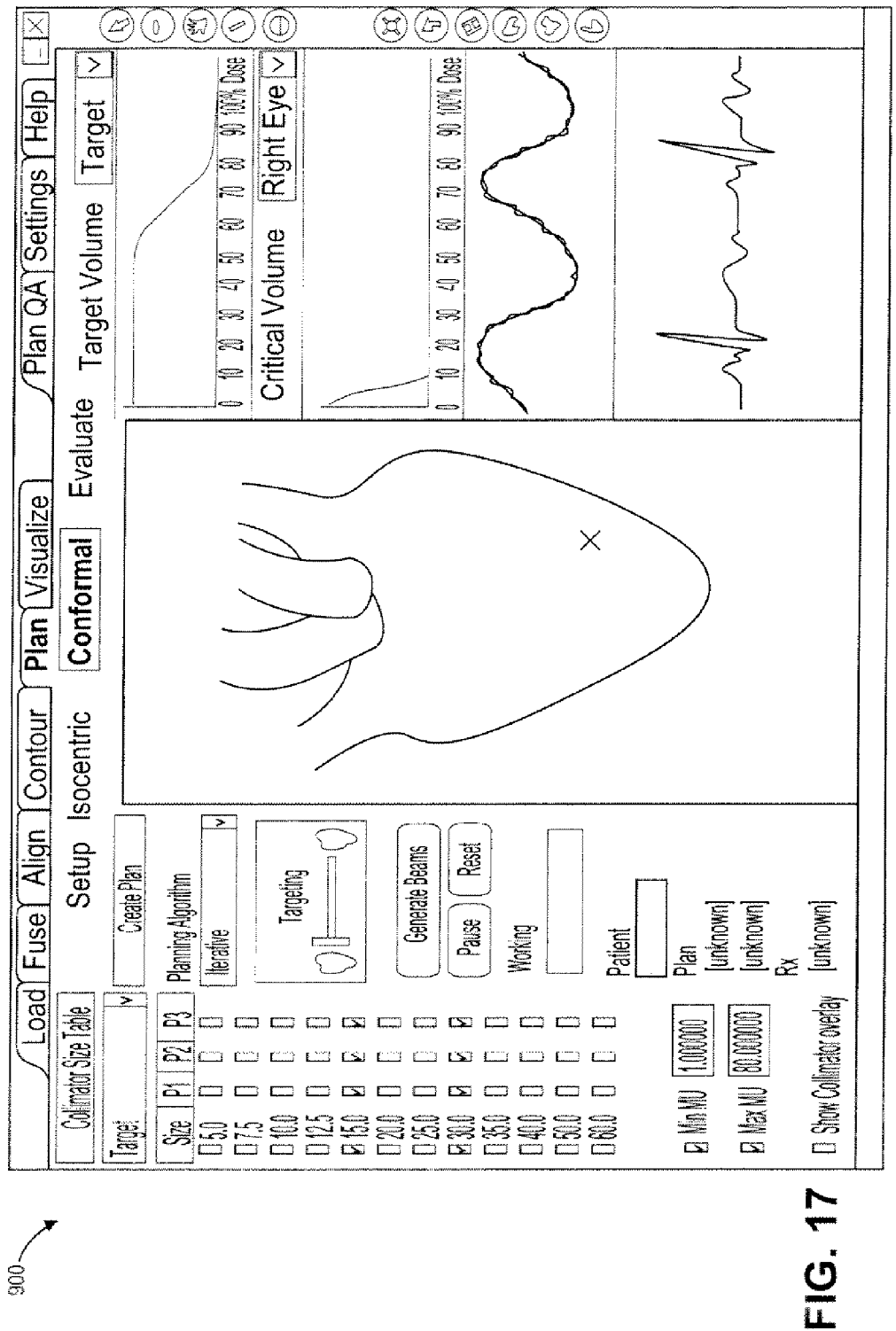
FIG. 17 is a schematic view of an exemplary user interface in accordance with one embodiment of the invention.

FIG. 17 is an exemplary screen shot of a user interface 900 in accordance with one embodiment of the invention. The user interface 900 may show the target location, treatment parameters and the like.

The embodiments described herein may be used to accurately track the motion of a moving target region (pathological anatomy) in the human anatomy, due to other patient motions during the treatment. The embodiments described herein may be used to treat atrial fibrillation, for example, where the target is located in those areas in which the formation of lesions would be therapeutic. In particular, the target is located in those areas in which the formation of lesions would cure atrial fibrillation by properly directing electrical impulses to the AV node and onto the ventricles. Because the target undergoes motion due to respiration and cardiac pumping, the embodiments described herein track the target with sufficient precision to create the lesions to inhibit atrial fibrillation.

It should be noted in particular that although discussed herein in regards to a robotic-based, image guided radiation treatment system, the methods herein may also be used with other types of radiation treatment systems such as a gantry based radiation delivery system. It should also be noted that the methods and apparatus are discussed herein in relation to CT imaging for ease of explanation. The method and apparatus discussed herein may also be used to develop treatment plans using other types of 4D medical diagnostic images (anatomical and/or functional), for example, magnetic resonance (MR), ultrasound (US), nuclear medicine (NM) positron emission tomography (PET) and single photon emission computed tomography (SPECT), etc. In addition, the "target regions" discussed herein may include an anatomical feature(s) of a patient such as a pathological or normal anatomy and may include one or more non-anatomical reference structures. Alternatively, a target region need not include an anatomical structure in embodiments outside the field of medical diagnostic imaging and patient treatment.

In the foregoing specification, the invention has been described with reference to specific exemplary embodiments thereof. It will, however, be evident that various modifications and changes may be made thereto without departing from the broader spirit and scope of the invention as set forth in the appended claims. The specification and drawings are, accordingly, to be regarded in an illustrative sense rather than a restrictive sense.

What is claimed is:

1. A method of tracking cardiac targets comprising:
   receiving a cardiac pumping signal;
   receiving a respiratory signal;
   receiving a radiation treatment plan developed using four dimensional image data;
   developing a cardiac motion model of a cardiac target using the cardiac pumping signal, the respiratory signal and the four dimensional image data;
   identifying a blurring effect of cardiac motion on a dose distribution in the radiation treatment plan,
   generating a modified radiation treatment plan that takes into account the identified blurring effect; and
   delivering radiation in accordance with the modified radiation treatment plan.

2. The method of claim 1, wherein delivering radiation comprises tracking the radiation delivery based on a correction generated from the cardiac pumping signal.

3. The method of claim 1, wherein delivering radiation comprises moving the radiation beam based on the respiratory signal of the cardiac target.

4. The method of claim 1, wherein delivering radiation comprises tracking the radiation delivery based on a correction generated from the cardiac pumping signal and moving the radiation beam based on the respiratory signal of the cardiac target.

* * * * *